United States Patent
Pruss et al.

(10) Patent No.: US 9,447,140 B2
(45) Date of Patent: Sep. 20, 2016

(54) CHOLEST-4-EN-3-ONE OXIME DERIVATIVES, PHARMACEUTICAL COMPOSITIONS CONTAINING SAME, AND PREPARATION METHOD

(75) Inventors: Rebecca Pruss, Cassis (FR);
Abdesslame Nazih, Marseilles (FR);
Corinne Chaimbault, Marseilles (FR);
Cyrillo Drouot, Draguignan (FR)

(73) Assignee: TROPHOS, Marseilles (FR)

( * ) Notice: Subject to any disclaimer, the term of this patent is extended or adjusted under 35 U.S.C. 154(b) by 507 days.

(21) Appl. No.: 13/056,867

(22) PCT Filed: Jul. 29, 2009

(86) PCT No.: PCT/FR2009/000944
§ 371 (c)(1),
(2), (4) Date: May 23, 2011

(87) PCT Pub. No.: WO2010/012904
PCT Pub. Date: Feb. 4, 2010

(65) Prior Publication Data
US 2011/0224180 A1   Sep. 15, 2011

(30) Foreign Application Priority Data

Jul. 30, 2008 (FR) .................................... 08 04338

(51) Int. Cl.
*A61K 31/575* (2006.01)
*A61K 31/58* (2006.01)
*C07J 41/00* (2006.01)
*C07J 43/00* (2006.01)

(52) U.S. Cl.
CPC ........... *C07J 41/0016* (2013.01); *C07J 43/003* (2013.01)

(58) Field of Classification Search
CPC ........................ C07J 41/0016; C07J 43/003
USPC ................... 552/520; 540/108; 514/169, 176
See application file for complete search history.

(56) References Cited

FOREIGN PATENT DOCUMENTS

WO   WO 2004082581   *   9/2004

OTHER PUBLICATIONS

Frelek et al., "Chiroptical Properties of Stereoisomeric Conjugated Oximes, I.", Liebigs Ann. Chem. 1991, pp. 89-91.*

* cited by examiner

*Primary Examiner* — Barbara P Badio
(74) *Attorney, Agent, or Firm* — Browdy and Neimark, PLLC

(57) ABSTRACT

The present invention relates to novel chemical compounds, in particular cholest-4-en-3-one oxime derivatives and to the use thereof as medicaments, especially as cytoprotective medicaments, in particular neuroprotective, cardioprotective and/or hepatoprotective medicaments.

29 Claims, No Drawings

CHOLEST-4-EN-3-ONE OXIME DERIVATIVES, PHARMACEUTICAL COMPOSITIONS CONTAINING SAME, AND PREPARATION METHOD

The present invention relates to novel chemical compounds, particularly cholest-4-en-3-one oxime derivatives, their use as medicaments, in particular as cytoprotective medicaments, particularly as neuroprotective, cardioprotective and/or hepatoprotective medicaments.

Said medicaments are particularly suited to the pathologies and traumas associated with cell degeneration or death, particularly those of motor neurons and/or cardiomyocytes and/or hepatocytes.

The invention also relates to the pharmaceutical compositions containing said compounds, and their preparation method.

The cell degenerative processes are characterized by the dysfunction of the cells often leading to undesirable cell activities and cell death.

Cells have developed adaptation mechanisms, in response to stress, which prolong their life time or delay or prevent cell death (cytoprotective mechanisms).

However, these cytoprotective mechanisms are sometimes insufficient, inadequate, or induced too late to be effective and the cells die. It may therefore prove useful to have novel cytoprotective medicaments available, which would promote cytoprotection.

Among the main cell death mechanisms, a distinction is essentially drawn between necrosis, apoptosis and necroptosis.

Necrosis is a so-called "accidental" cell death which occurs during tissue damage. It is the cell's plasma membrane which is most affected, leading to a modification of the cell homeostasis. The cells will become gorged with water to the point that this leads to lysis of their plasma membrane. This cell lysis leads to the release of the cytoplasmic content into the surrounding medium. Necrosis is at the origin of the inflammatory process.

Necrosis can affect a set of cells or a tissue whilst the other neighbouring parts remain alive. The transformation which results from this is mortification of the cells or the tissues.

In other words, necrosis is defined by morphological modifications occurring when a cell reaches the end of its life following events such as a major trauma such as a stoppage or reduction of the blood circulation in an organ, hyperthermia (significant rise in temperature), intoxication with a chemical product, a physical shock, etc.

One of the best-known necroses is that of the myocardium during infarction (interruption to the blood supply to the cardiac muscle) due to an obliteration (obstruction) of a coronary artery.

Apoptosis forms an integral part of the normal physiology of an organism. This is a highly regulated physiological form of cell death and it is necessary to the survival of the multicellular organisms. Apoptosis is a process which is of vital importance to embryogenesis.

The cells undergoing apoptosis, or apoptotic cells, become isolated from the other cells. Apoptosis usually involves individual cells in a tissue and does not cause inflammation. One of the morphological points characteristic of apoptosis is the significant condensation both of the nucleus and of the cytoplasm which causes a significant reduction in cell volume. The nucleus then becomes fragmented, each fragment is surrounded by a double envelope. Apoptotic bodies (cytoplasmic and nuclear elements) are then released and will be absorbed by the neighbouring cells by phagocytosis.

Apoptosis can be induced in different ways. For example, radiation, the presence of a chemical compound or a hormone are stimuli capable of inducing a cascade of apoptotic events in the cell. Intracellular signals such as incomplete mitosis or damage to DNA can also induce apoptosis.

Apoptosis also occurs after the action of a genotoxic agent or in the course of a disease. Certain pathologies are characterized by abnormal apoptosis, leading to the loss of certain cell populations, such as for example hepatotoxicity, retinopathies, cardiotoxicity.

A distinction is therefore drawn between physiological apoptosis and pathological apoptosis. The invention essentially addresses pathological apoptosis.

There are other cell death mechanisms, such as for example necroptosis, which exhibit characteristics of necrosis and apoptosis. A cell dying by necroptosis exhibits characteristics similar to those of a cell dying by necrosis, but the biochemical stages of this mechanism are more similar to those of apoptosis. This cell death mechanism occurs for example in ischaemia.

It is therefore also one of the purposes of the present invention to make available novel medicaments which could make it possible to prevent and/or treat necrosis and/or pathological apoptosis and/or necroptosis (antinecrotic and/or antiapoptotic and/or antinecroptotic medicaments).

The cell degenerative processes can result, inter alia, from pathological situations collectively termed degenerative diseases or conditions, from traumas, or from exposure to various factors.

These traumas and factors can include, for example, exposure to radiation (UV, gamma), hypoxia or oxygen deficiency, nutrient deficiency, growth factor deficiency, poisons, cell toxins, waste, environmental toxins, free radicals, reactive oxygen species. Chemical or biological agents used as therapeutic agents in the context of medical treatments such as for example cytostatic agents or anti-inflammatory agents may also be mentioned.

The most significant pathological situations characterized by a degenerative process include:
- diseases of the bones, joints, connective tissue and cartilage, such as osteoporosis, osteomyelitis, arthritis including for example osteoarthritis, rheumatoid arthritis and psoriatic arthritis, avascular necrosis, progressive ossifying fibrodysplasia, rickets, Cushing's syndrome;
- muscle diseases such as muscular dystrophy, such as for example Duchenne's muscular dystrophy, myotonic dystrophies, myopathies and myasthenias;
- skin diseases, such as dermatitis, eczema, psoriasis, ageing, or also cicatrization changes;
- cardiovascular diseases such as cardiac and/or vascular ischaemia, myocardial infarction, ischaemic cardiopathy, chronic or acute cardiac failure, cardiac dysrhythmia, atrial fibrillation, ventricular fibrillation, paroxystic tachycardia, cardiac failure, anoxia, hypoxia, side effects of therapies with anticancer agents;
- circulatory diseases such as atherosclerosis, arteriosclerosis, peripheral vascular diseases, cerebral vascular accidents, aneurysms;
- haematological and vascular diseases such as: anaemia, vascular amyloidosis, haemorrhage, sickle-cell anaemia, erythrocyte fragmentation syndrome, neutropenia, leukopenia, medullary aplasia, pancytopenia, thrombocytopenia, haemophilia;

lung diseases including pneumonia, asthma; chronic obstructive lung diseases such as for example chronic bronchitis and emphysema;

diseases of the gastro-intestinal tract, such as ulcers;

liver diseases including viral hepatitis and cirrhosis, liver diseases caused by toxins or medicaments, conditions which can lead to cirrhosis such as non-alcoholic steatohepatitis (NASH), Wilson's disease, primitive sclerosing cholangitis, or primitive biliary cirrhosis diseases of the pancreas such as for example acute or chronic pancreatitis;

metabolic diseases such as diabetes mellitus and insipidus, thyroiditis;

kidney diseases such as for example acute renal disorders or glomerulonephritis;

viral and bacterial infections such as septicaemia;

severe intoxications with chemical agents, toxins or medicaments;

degenerative conditions associated with Acquired Immune Deficiency Syndrome (AIDS);

disorders associated with ageing, such as accelerated ageing syndrome;

inflammatory diseases, such as Crohn's disease, rheumatoid arthritis;

auto-immune diseases such as lupus erythematosus;

dental disorders such as those leading to degradation of the tissues such as for example periodontitis;

opthalmic diseases or disorders including diabetic retinopathies, glaucoma, macular degenerations, retinal degeneration, retinitis pigmentosa, retinal holes or tears, detached retina, retinal ischaemia, acute retinopathies associated with trauma, inflammatory degenerations, post-surgery complications, drug-induced retinopathies, cataract;

disorders of the auditory pathways, such as otosclerosis and antibiotic-induced deafness;

diseases associated with mitochondria (mitochondrial pathologies), such as Friedrich's ataxia, congenital muscular dystrophy with structural mitochondrial anomalies, certain myopathies (MELAS syndrome, MERFF syndrome, Pearson syndrome), MIDD syndrome (maternally inherited diabetes and deafness), Wolfram syndrome, dystonia.

Moreover, the neurodegenerative processes are characterized by the dysfunction and death of neurons leading to the loss of neurological functions mediated by the brain (central nervous system, CNS), the spinal cord and the peripheral nervous system (PNS). They can result, inter alia, from pathological situations collectively termed neurodegenerative diseases or conditions, from trauma, or from exposure to toxins.

The most significant pathologies which are characterized by a neurodegenerative process are:

chronic neurodegenerative diseases, in particular chronic demyelinating diseases, hereditary or sporadic, advantageously Alzheimer's disease, Huntington's disease, Parkinson's disease, amyotrophic lateral sclerosis, spinal amyotrophies, particularly infantile, Creutzfeldt-Jakob's disease, multiple sclerosis, amyotrophic lateral scleroses, leukodystrophies including adrenoleukodystrophy, epilepsy, dementia, schizophrenia, and the neurological syndromes associated with AIDS;

neuronal lesions linked with ageing;

peripheral neuropathies which are hereditary or resulting from a lesion, such as Fabry's disease, Charcot-Marie-Tooth disease, Krabbe disease, leukodystrophies, diabetic neuropathies and those caused by anticancer treatments;

traumas of the brain, the peripheral nerves or the spinal cord;

ischaemias of the brain or the spinal cord following a cerebro-vascular accident, or caused by a lack of blood irrigation;

degenerations which are hereditary, resulting from a lesion or linked with ageing of the sensory neurons of vision, such as macular degeneration, pigmentary retinitis, or degeneration of the optic nerve induced by glaucoma;

degenerations which are hereditary, traumatic or linked with ageing of the sensory neurons of hearing leading to a reduction or a loss of audition.

Some of the signalling pathways affected in these pathologies are common to a large number of neurodegenerative diseases. Alzheimer's disease is the most frequent dementia. It causes the appearance of atrophy of the brain, a predominant neuronal loss in the hippocampus and it also affects the cholinergic neurons. Other pathologies, such as the lobar atrophies (Pick's disease, Creutzfeld-Jakob's disease), Lewy body dementia, vascular dementias, Parkinson's disease are associated with significant neuronal death at the origin of the symptoms of these dementias.

A therapeutic approach for protecting the neurons from dying is the supply of neurotrophic proteins.

These proteins, such as BDNF (brain-derived neurotrophic factor), CNTF (ciliary neurotrophic factor), NGF (nerve growth factor), GDNF (glia-derived neurotrophic factor) are synthesized during embryonal development or after lesion in adults. These growth factors encourage the survival, maturation and differentiation of neuronal cells. Moreover, they inhibit the apoptotic mechanisms, activate multiple survival pathways and protect a large number of neuronal populations. Their use is proposed in the majority of neuronal degenerations.

Compounds which would activate the expression of neurotrophic factors or which would mimic the action of these factors have a therapeutic potential for the treatment of neurodegenerative syndromes.

In particular, the supply of neurotrophic molecules for the treatment of neuronal degenerations has three objectives:

to compensate for a potential deficiency in neurotrophic factors linked to a failure of supply by the peripheral or central targets of the neurons and/or a problem with the retrograde transport of these factors;

to intervene in a non-specific fashion on biochemical pathways involved in the degenerative cascade;

to promote the natural compensator phenomena of dendritic growth and arborization of the nerve endings.

These compounds would therefore have a beneficial effect in a large number of pathologies in particular in the pathologies affecting the peripheral and central nervous systems.

Moreover, within the above context, the motor neurons are neurons in particular present in the spinal cord and the brain stem. Their degeneration or their death can lead to a progressive weakening of the muscles of the limbs, then to atrophy and possibly to spasticity (i.e. a permanent contraction) of the muscle.

The most important pathologies which result from the degeneration and death of the spinal and/or bulbar motor neurons are amyotrophic lateral sclerosis, also known by the name of Charcot's disease or also Lou Gehrig's disease, and spinal amyotrophies, particularly infantile, also known by the names of Werdnig-Hoffmann disease or Kugelberg-Welander disease.

Moreover, a degeneration of the motor neurons is observed in the case of traumas with crushing and/or section of the spinal cord or the peripheral motor nerves.

More generally, spinal amyotrophies are referred to as diseases where the degeneration or death of motor neurons of the spinal cord are involved.

Amyotrophic lateral sclerosis (ALS) is a neurodegenerative disease associated with different types of inclusions such as Lewis bodies and characterized by a degeneration of the spinal and cortical motor neurons the fatal outcome of which is sometimes associated with frontal dementia. During the development of ALS, the degenerative phenomena occur not only in the brain but also in the spinal cord and consequently in the muscle, by lack of innervation.

With regard to chemical structures, the literature provides a few examples of 3-oxyimino-cholest-4-ene derivatives. This is the case in particular with patent applications WO2004/082581 and WO2007/118967 describing 3-oxyimino-cholest-4-ene and its derivatives for their neuroprotective and cytoprotective properties respectively.

The document Liebig's *Annalen der Chemie* [(1991), (1), pages 89-91], describes the compounds 3-oxyimino-4-chloro-cholest-4-ene and 3-oxyimino-4-bromo-cholest-4-ene as well as their chiroptic property. But this document describes no cytoprotective, neuroprotective and/or cardioprotective activity for these two compounds.

The document Chemical & Pharmaceutical Bulletin [(1972), 20(7), pages 1567-9], describes the anti-isomer of 3-oxyimino-4-methyl-cholest-4-ene, without however describing or mentioning any cytoprotective, neuroprotective, and/or cardioprotective activities for this compound.

Without however disparaging the treatments known at present, to date there is no effective treatment for stopping cell degeneration, particularly neuronal degeneration.

Thus, there is still a real need for novel products making it possible to effectively protect cells from degeneration phenomena.

The compounds of the present invention, apart from the fact that they are novel, exhibit very useful pharmacological properties.

They prove to be advantageously cytoprotective, particularly neuroprotective and/or cardioprotective and/or hepatoprotective.

In addition to their biological activity, certain novel compounds can also exhibit advantageous properties in relation to their pharmacological activity, such as their pharmacokinetics, bioavailability, solubility, stability, toxicity, absorption and/or metabolism. This makes them very useful for preparing a medicament, particularly for preparing a cytoprotective, very particularly neuroprotective and/or cardioprotective and/or hepatoprotective medicament.

More specifically, a subject of the present invention is the novel compounds corresponding to formula (I):

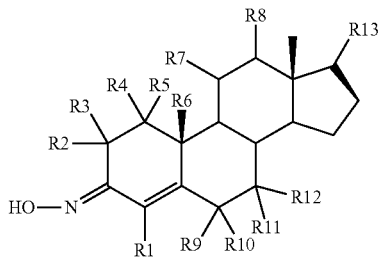

(I)

in which, $R_1$ can represent a hydrogen atom or a $C_1$-$C_6$ alkyl, $C_3$-$C_6$ cycloalkyl, $C_2$-$C_6$ alkenyl, $C_2$-$C_6$ alkynyl, aryl group, a heterocycle, or a halogen atom or a —CN, —CF$_3$, —NO$_2$, —OR$^a$, —SR$^a$, —SO$_2$R$^a$, —NR$^a$R$^b$, —OC(O)R$^a$, —OC(O)NR$^a$R$^b$, —C(O)OR$^a$, —CONR$^a$R$^b$ group in which (i) R$^a$ and R$^b$, simultaneously or independently of each other, can be chosen from a hydrogen atom or a $C_1$-$C_6$ alkyl, $C_3$-$C_6$ cycloalkyl, aryl, heteroaryl group or (ii) R$^a$ and R$^b$ can together form a linear or branched hydrocarbon chain having 2 to 6 carbon atoms, optionally comprising one or more double bonds and/or optionally interrupted by one or more oxygen, sulphur or nitrogen atom(s), $R_2$ can represent a hydrogen atom, or a $C_1$-$C_6$ alkyl, $C_3$-$C_6$ cycloalkyl, aryl group or a halogen atom;

$R_3$ can represent a hydrogen atom, or a $C_1$-$C_6$ alkyl group or a halogen atom or a —CN, —OR$^a$, —SR$^a$, —Is, —COOR$^a$, —NR$^a$R$^b$, —OCONR$^a$R$^b$ group, —R$^a$ and —R$^b$ being as defined previously; or $R_3$ and $R_2$ together with the carbon to which they are attached, can form a ($C_3$-$C_6$)-cycloalkyl group;

$R_4$ can represent a hydrogen atom, or a $C_1$-$C_6$ alkyl group; or $R_4$ and $R_2$ can together form an additional carbon-carbon bond (C=C bond) between the carbon atoms to which $R_2$ and $R_4$ are attached, or a $C_3$-$C_6$ cycloalkyl group;

$R_5$ can represent a hydrogen atom or an —OR$^a$, —SR$^a$, —CN, —NR$^a$R$^b$ group, —R$^a$ and —R$^b$ being as defined previously, $R_6$ can represent a hydrogen atom or a —CH$_3$, —CH$_2$—CN, —CH$_2$—SR$^a$, —CH$_2$—SeR$^a$ group or also a group corresponding to formula (A) or (B) below:

$$—CH_2-Q-R^c \quad (A)$$

or $$C(O)-Q-R^c \quad (B)$$

in which

Q can represent an oxygen atom or an —NR$^a$ group in which R$^a$ is as defined previously, or a spacer arm constituted by a linear or branched hydrocarbon chain, optionally substituted, comprising 2 to 20 carbon atoms and also comprising at least one heteroatom, R$^c$ can represent a hydrogen atom or a $C_1$-$C_6$ alkyl, aryl, heteroaryl group, a heterocycle, $C_1$-$C_6$ alkyl-C(O)—, aryl-C(O)—, heteroaryl-C(O)—, heterocycle-C(O)—, in particular a group represented by one of formulae (C) or (D)

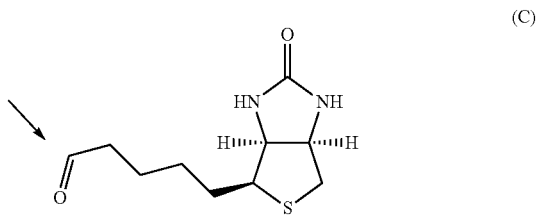

(C)

-continued

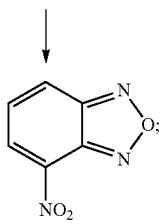
(D)

R$_7$ can represent a hydrogen atom or a halogen atom or a hydroxy group, preferentially a hydrogen atom;

R$_8$ can represent a hydrogen atom, or an —OR$^a$ group, R$^a$ being as defined previously, preferentially a hydrogen atom;

R$_9$ can represent a hydrogen atom, or a C$_1$-C$_6$ alkyl, C$_3$-C$_6$ cycloalkyl, C$_2$-C$_5$ alkenyl, C$_2$-C$_6$ alkynyl, aryl group or a halogen atom, preferentially a hydrogen atom;

R$_{10}$ can represent a hydrogen atom, or a C$_1$-C$_6$ alkyl group, a halogen atom or a —CN, —CF$_3$, —NO$_2$, —OR$^a$, —SR$^a$, —SO$_2$R$^a$, —NR$^a$R$^b$, —OC(O)R$^a$, —OC(O)NR$^a$R$^b$, —C(O)OR$^a$, —C(O)NR$^a$R$^b$ group, R$^a$ and R$^b$ being as defined previously, preferentially a hydrogen atom;

R$_{10}$ can represent, together with R$_9$, an oxo, =CH—C$_1$-C$_6$ alkyl, =CH-aryl, =CH—C$_3$-C$_6$ cycloalkyl group;

R$_{11}$ can represent a hydrogen atom or a C$_1$-C$_6$ alkyl, C$_3$-C$_6$ cycloalkyl or aryl group; preferentially a hydrogen atom or R$_{11}$ and R$_9$ can together form an additional C—C bond between the carbon atoms to which they are attached, or can together form a C$_3$-C$_6$ cycloalkyl group;

R$_{12}$ can represent a hydrogen atom or a C$_1$-C$_6$ alkyl group, or an —OR$^a$, —SR$^a$ group, —R$^a$ being as defined previously, preferentially a hydrogen atom R$_{13}$ can represent
(i) a C$_4$-C$_{12}$ alkyl group or a C$_4$-C$_{12}$ alkenyl group, in particular a group chosen from

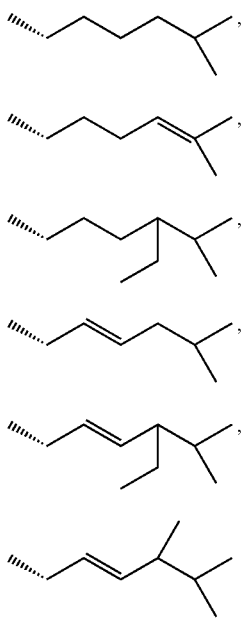

or (ii) a group corresponding to formula E below:

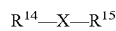
(E)

In which:

R$^{14}$ can represent a C$_4$-C$_{12}$ alkyl group or a C$_4$-C$_{12}$ alkenyl group, in particular a alkyl group, preferentially the following G$_7$ group

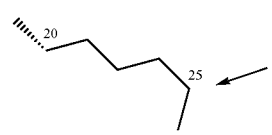

and

X can represent an oxygen atom or an —NR$^a$ group with R$^a$ being as described previously, and R$^{15}$ can represent a C$_1$-C$_6$ alkyl, C$_3$-C$_6$ cycloalkyl, aryl, heteroaryl group, heterocycle, —C(O)—C$_1$-C$_6$ alkyl, cycloalkyl, —C(O)-aryl, —C(O)-heteroaryl, —C(O)-heterocycle, in particular a group represented by formula (C) or (D) as described previously:

as well as:
its SYN and ANTI isomers, when they exist,
its optical isomers (enantiomers, diastereoisomers), when they exist,
its addition salts with a pharmaceutically acceptable acid or base,
its hydrates and its solvates,
its prodrugs, with the exception, of the following compounds:
3-oxyimino-cholest-4-ene;
3-oxyimino-2,2-dimethyl-cholest-4-ene;
3-oxyimino-7,7-dimethyl-cholest-4-ene;
3-oxyimino-2-(3-oxyimino-butyl)-cholest-4-ene;
3-oxyimino-cholest-1,4-diene;
3-oxyimino-cholest-4,6-diene;
3-oxyimino-cholest-4,22-diene;
3-oxyimino-cholest-4,24-diene;
3-oxyimino-cholest-4-en-6-one;
3-oxyimino-24-methyl-cholest-4,22-diene;
3-oxyimino-24-methyl-cholest-4,22-dien-6-one;
3-oxyimino-24-ethyl-cholest-4-ene;
3-oxyimino-24-ethyl-cholest-4-en-6-one;
3-oxyimino-24-ethyl-cholest-4,22-diene;
3-oxyimino-24-ethyl-cholest-4,22-dien-6-one;
3-oxyimino-cholest-4,22-dien-6-one;
3-oxyimino-cholest-4,24-dien-6-one;
3,6-dioxyimino-cholest-4-ene;
3,6-dioxyimino-cholest-4,22-diene;
3,6-dioxyimino-cholest-4,24-diene;
3,6-dioxyimino-24-methyl-cholest-4,22-diene;
3,6-dioxyimino-24-ethyl-cholest-4-ene;
3,6-dioxyimino-24-ethyl-cholest-4,22-diene;
3-oxyimino-4-chloro-cholest-4-ene;
3-oxyimino-4-bromo-cholest-4-ene;
3-oxyimino-4-methyl-cholest-4-ene;
3-oxyimino-6-ethoxy-cholest-4,6-diene
3-oxyimino-cholest-1,4,6-triene.

It being understood that according to the present text,
the term "C$_1$-C$_6$ alkyl" refers to a linear or branched hydrocarbon radical, comprising 1 to 6 carbon atoms, such as methyl, ethyl, propyl, isopropyl, butyl, isobutyl, tert-butyl, pentyl, neopentyl, n-hexyl. The C$_1$-C$_4$ alkyl groups are preferred. The alkyl groups can optionally be substituted by an aryl group as defined hereafter, in which case the term arylalkyl group is used. Examples of arylalkyl groups are in particular benzyl and phenethyl. Optionally, the alkyl groups can be substituted once or several times by one of the substituents chosen independently from a halogen atom or a —CN, —CF$_3$, —COOR$^a$, —CONR$^a$R$^b$, —O—CONR$^a$R$^b$, —NR$^a$R$^b$, —OR$^a$, —SR$^b$ group, the R$^a$ and R$^b$ groups being as described previously. Unless otherwise specified, the hydrocarbon radical can comprise 4 to 12 carbon atoms. The term "C$_2$-C$_6$ alkenyl" refers to a linear or branched or cyclic hydrocarbon radical, comprising one or more double-bonds having 2 to 6 carbon atoms. The ethenyl, 1-propenyl, 2-propenyl, 1-butenyl, 2-butenyl, 1-pentenyl, 2-pentenyl, 3-methyl-3-butenyl, 1-hexenyl radicals may be mentioned for example. Optionally, the alkenyl groups can be substituted once or several times by one of the substituents chosen independently from a halogen atom or a —CN, —CF$_3$, —COOR$^a$, —C(O)NR$^a$R$^b$, —O—C(O)NR$^a$R$^b$, —NR$^a$R$^b$, —OR$^a$, —SR$^b$ group, the R$^a$, R$^b$ groups being as described previously;

the term "C$_3$-C$_6$ cycloalkyl" refers to a saturated or partially unsaturated cyclic hydrocarbon radical having 3 to 6 carbon atoms. The cycloalkyl groups include in particular the substituents cyclopropyl, cyclobutyl, cyclopentyl, cyclopentyl, cyclohexyl, cyclohexenyl. Optionally, the cycloalkyl groups can be substituted once or several times by one of the substituents chosen independently from a halogen atom or a —CN, —CF$_3$, —COOR$^a$, —C(O)NR$^a$R$^b$, —O—C(O)NR$^a$R$^b$, —NR$^a$R$^b$, —OR$^a$, —SR$^a$ group, the R$^a$, R$^b$ group being as described previously;

the term "C$_2$-C$_6$ alkynyl" refers to a linear or branched hydrocarbon radical comprising at least one triple bond having 2 to 6 carbon atoms. The alkynyl groups include in particular the substituents ethynyl, 1-propynyl, 2-propynyl, 1-butynyl, 2-butynyl, 1-pentynyl or 2-pentynyl. Optionally, the alkynyl groups can be substituted once or several times by one of the substituents chosen independently from a halogen atom or a —CN, —CF$_3$, —COOR$^a$, —C(O)NR$^a$R$^b$, —O—C(O)NR$^a$R$^b$, —NR$^a$R$^b$, —OR$^a$, —SR$^a$ group, the R$^a$, R$^b$ group being as described previously;

the term "C$_6$-C$_{10}$ aryl" refers to an aromatic hydrocarbon radical having 6 to 10 carbon atoms, even more preferentially 6 carbon atoms. The aryl groups include in particular the phenyl, naphthyl and bi-phenyl radicals. Optionally, the aryl groups can be substituted once or several times by one of the substituents chosen independently from a halogen atom or an alkyl, —CN, —CF$_3$, —N$_3$, —NO$_2$, —COOR$^a$, —C(O)NR$^a$R$^b$, —O—C(O)NR$^a$R$^b$, —NR$^a$R$^b$, —OR$^a$, —SR$^a$ group, the R$^a$, R$^b$ groups being as described previously;

the term "C$_3$-C$_9$ heterocycle" refers to a saturated, unsaturated or aromatic mono- or polycyclic radical, optionally substituted, comprising 3 to 9 carbon atoms and comprising one or more heteroatoms. Preferably, the heteroatoms are chosen from oxygen, sulphur and nitrogen. Examples of heterocycles are the furyl, thienyl, pyrrole, imidazole, isothiazole, thiazole, isoxazole, oxazole, pyridine, pyrazine, pyrimidine, pyridazine, indole, isoindole, indazole, quinoline, isoquinoline, phthalazine, quinazoline, pyrrolidine, imidazolidine, pyrrazolidine, piperidine, piperazine, morpholine, thiazolidine or phthalimide, benzimidazole radicals.

Optionally, the heterocyclic groups can be substituted once or several times by one of the substituents chosen independently from a halogen atom or an alkyl, —CN, —CF$_3$, —N$_3$, —NO$_2$, —COOR$^a$, —C(O)NR$^a$R$^b$, —O—C(O)NR$^a$R$^b$, —NR$^a$R$^b$, —OR$^a$, —SR$^a$ group, the R$^a$, R$^b$ groups being as described previously;

the term "halogen" refers to a chlorine, bromine, fluorine and iodine atom. Preferably a fluorine atom;

the expression "spacer arm" refers to a hydrocarbon chain comprising 2 to 20 carbon atoms, saturated or not, optionally substituted and comprising at least one heteroatom. In particular said spacer arm is chosen from the following K1, K2, K3 or K4 groups in which R$^a$ is as described previously;

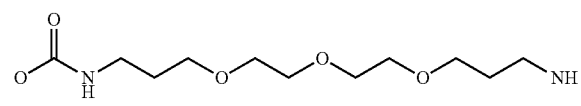

K1

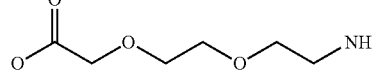

K2

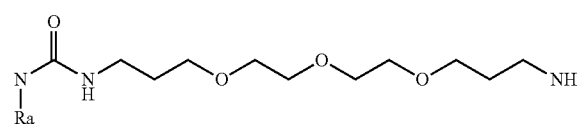

K3

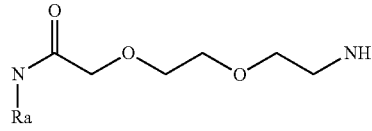

K4 the term "treatment" denotes preventative, curative or palliative treatment, as well as the management of patients (reduction of suffering, improvement in life expectancy, slowing down of the progression of the disease), etc. The treatment can moreover be carried out in combination with other ingredients or treatments, such as in particular other active ingredients for treating the pathologies or traumas specified in the present Application;

the term "cytoprotective" refers to the ability of agents, for example chemical compounds, natural or not, to maintain the interactions of cells with each other or with the other tissues, to protect cells from the degeneration phenomena leading to a loss of cell function or to undesirable cell activities, with or without cell death, and/or from cell dysfunctions and/or from the degenerative diseases or disorders leading to these cell dysfunctions, said dysfunctions or said diseases or conditions leading or not leading to cell death;

the terms "neuroprotective" or "cardioprotective" or "hepatoprotective" refer to the same properties of said agents but specifically for cells of the nervous system ("neuroprotective") either specifically for cells of the cardiac system ("cardioprotective"), or specifically for the cells of the hepatic system ("hepatoprotective"). It is therefore understood that a cytoprotective or neuroprotective or cardioprotective or hepatoprotective compound is a compound which has the properties described previously.

Particularly preferred compounds of formula (I) are those in which:
- the substituent $R_1$ can be chosen from the hydrogen atom, the fluorine atom, the $C_1$-$C_6$ alkyl group, optionally a $C_1$-$C_4$ alkyl group and a phenyl group, optionally substituted;
- the substituent $R_6$ can be chosen from a —$CH_3$ group and a —$CH_2$—OH group, even more preferentially, the substituent $R_6$ can represent a —$CH_3$ group.

According to another aspect of the invention, the preferred substituent $R_6$ can represent a group corresponding to formula (A) below:

—$CH_2$-Q-$R^c$        (A)

in which Q can represent an oxygen atom and $R^c$ can represent the group corresponding to formula (C) below

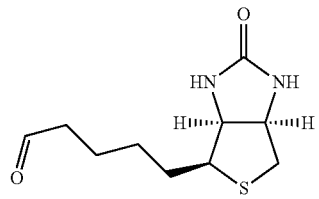

(C)

Other preferred compounds according to the invention are those for which the substituent $R_6$ can represent a group corresponding to formula (A) below:

—$CH_2$-Q-$R^c$        (A)

in which Q can represent an $NR^a$ group, $R^a$ being as described previously, and $R^c$ can represent a group chosen from aryl, heteroaryl, heterocycle, in particular the group corresponding to formula (D) below:

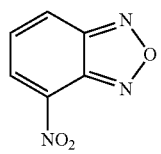

(D)

The compounds for which $R_4$ together with $R_2$, forms an additional C—C bond between the carbon atoms to which $R_2$ and $R_4$ are attached, are also preferred.

Similarly, the compounds corresponding to formula (I) in which $R_{11}$ and $R_9$ together form an additional C—C bond between the carbon atoms to which they are attached, are also preferred compounds.

The particularly preferred substituent $R_{13}$ according to the invention is chosen from the following G1 and G2 groups:

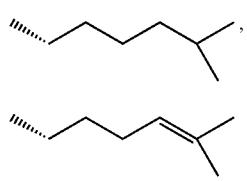

$G_1$ $G_2$

Other preferred compounds according to the invention are the compounds for which $R_{13}$ can represent a group corresponding to formula (E) below:

$R_{14}$—X—$R_{15}$        (E)

In which:
$R_{14}$ can represent the following $G_7$ group:

$G_7$

X can represent —NH or —$NCH_3$, and
(i) $R_{15}$ can represent a group chosen from an aryl, heteroaryl, heterocyclic group, in particular the group corresponding to formula (D) below

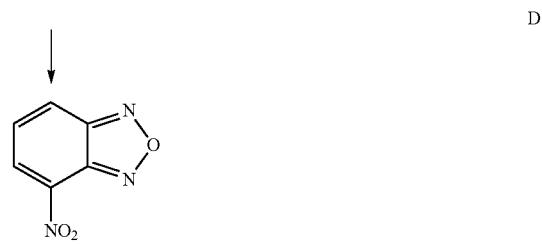 [SMILES: O=[N+]([O-])c1cccc2nonc12]

D or
(ii) $R_{15}$ can represent a group chosen from a —C(O)—$C_1$-$C_6$ alkyl, —C(O)—$C_3$-$C_6$ cycloalkyl, —C(O)-aryl, —C(O)-heteroaryl, —C(O)-heterocyclic group, in particular the group corresponding to formula (C) below:

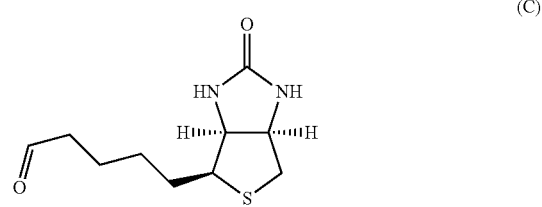 [SMILES: O=CCCCC[C@@H]1SC[C@@H]2NC(=O)N[C@@H]21]

(C)

Particularly advantageously, the preferred compounds according to the present invention are:
- 3-oxyimino-4-fluoro-cholest-4-ene;
- 3-oxyimino-6β-fluoro-cholest-4-ene;
- 3-oxyimino-2,2-difluoro-cholest-4-ene;
- 3-oxyimino-2,6-difluoro-cholest-4-ene;
- 3-oxyimino-2α-fluoro-cholest-4-ene;
- 3-oxyimino-25-[methyl(7-nitro-2,1,3-benzoxadiazol-4-yl)amino]-27-norcholest-4-ene;
- 3-oxyimino-25-((N-(+)-biotinoyl-N-methyl)amino)-27-norcholest-4-ene;
- 3-oxyimino-19-hydroxy-cholest-4-ene;
- 3-oxyimino-19-biotinyloxy-cholest-4-ene;
- 3-oxyimino-2-methyl-cholest-4-ene;
- 3-oxyimino-4-methoxy-cholest-4-ene;

as well as:

their SYN and ANTI isomers, when they exist, their optical isomers (enantiomers, diastereoisomers), when they exist, their addition salts with a pharmaceutically acceptable acid or base, their hydrates and their solvates, their prodrugs The addition salts with pharmaceutically acceptable acids can be for example salts formed with hydrochloric, hydrobromic, nitric, sulphuric, phosphoric, acetic, formic, propionic, benzoic, maleic, fumaric, succinic, tartaric, citric, oxalic, glyoxylic, aspartic or alkane sulphonic acids such as methane or ethane sulphonic acids, or arylsulphonic acids, such as benzene or paratoluene sulphonic acids, or carboxylic acids.

Certain preferred compounds of the present invention have one or more fluorine atoms. By way of example, 3-oxyimino-4-fluoro-cholest-4-ene (formula I-1) having a fluorine atom in position 4 is particularly preferred.

Formula I-1

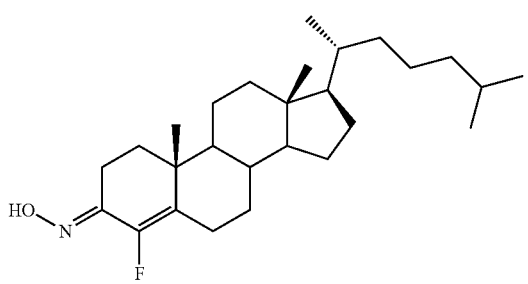

(I-1)

The introduction of such a fluorine atom into this compound surprisingly made it possible to modify its pharmacological properties. This fluorinated compound (formula I-1) obtained in the form of a single ANTI isomer, exhibits improved exposure when it is administered by oral route.

According to the present invention, 3-oxyimino-6-fluoro-cholest-4-en (formula I-2) and 3-oxyimino-2,2-difluoro-cholest-4-en (formula I-3) are among the preferred compounds.

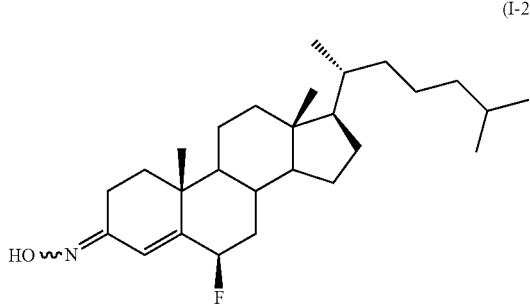

(I-2)

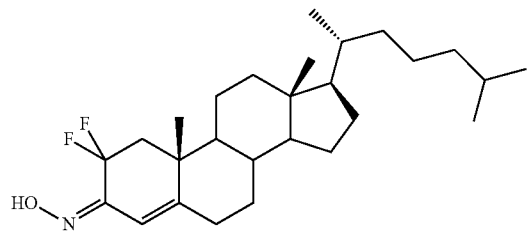

(I-3)

It should be noted that in the present text, the atom that can be represented by the general term "halogen", can also be a natural or synthetic, radioactive isotope such as for example in the case of fluorine, fluorine-18 ($^{18}$F). The radiolabelled compounds of formulae (I), particularly those labelled with the isotope $^{18}$F, are very useful for medical imaging, in particular for Positron Emission Tomography (PET) which is an in vivo imaging technique developed for the diagnosis of diseases, for example in the field of oncology, neurology and cardiology. Similarly in the case of bromine or iodine it may be mentioned that these can be represented by the radiolabelled isotopes bromine-75 ($^{78}$Br) and iodine-124 ($^{124}$I) respectively.

The general term "halogen" can also cover, according to the present text, the natural or synthetic, non-radioactive isotopes such as for example a non-radioactive isotope fluorine-19 ($^{19}$F), useful for biomedical research, and in particular in cognitive neuroscience and in particular for the Magnetic Resonance Imaging technique (MRI).

The compounds which are the subject of the present invention possess very useful pharmacological properties. They are endowed in particular with remarkable cytoprotective, particularly neuroprotective properties, very particularly vis-à-vis motor neurons, and cardioprotective and hepatoprotective properties.

These properties are illustrated hereafter in the experimental part. They justify the use of the compounds described above as well as that of their esters and/or of their addition salts with pharmaceutically acceptable acids, as cytoprotective medicaments, particularly as neuroprotective medicaments and/or cardioprotective and/or hepatoprotective medicaments.

Very particularly, the compounds according to the invention exhibit remarkable activity vis-à-vis motor neurons, neurons of the central nervous system, motor and peripheral nerves.

Thus, a subject of the invention is also the use as medicaments of compounds of formula (I), including 3-oxyimino-4-chloro-cholest-4-ene, 3-oxyimino-4-bromo-cholest-4-ene, 3-oxyimino-6-ethoxy-cholest-4,6-diene and 3-oxyimino-4-methyl-cholest-4-ene as well as their esters, and/or their addition salts with pharmaceutically acceptable acids.

A subject of the invention is therefore also the use of a compound of formula (I), including 3-oxyimino-4-chloro-cholest-4-ene, 3-oxyimino-4-bromo-cholest-4-ene, 3-oxyimino-6-ethoxy-cholest-4,6-diene and 3-oxyimino-4-methyl-cholest-4-ene or one of its esters, and/or of its addition salts with pharmaceutically acceptable acids, for preparing a cytoprotective medicament.

The compounds according to the present invention, because of their cytoprotective properties, can be used for preparing a medicament intended for the treatment or prevention of necrosis and/or of pathological apoptosis and/or of necroptosis (antinecrotic and/or antiapoptotic and/or antinecroptotic medicaments) or also for the treatment or prevention of conditions such as:

diseases of the bones, joints, connective tissue and cartilage, such as osteoporosis, osteomyelitis, arthritis including for example osteoarthritis, rheumatoid arthritis and psoriatic arthritis, avascular necrosis, progressive ossifying fibrodysplasia, rickets, Cushing's syndrome;

muscle diseases such as muscular dystrophy, such as for example Duchenne's muscular dystrophy, myotonic dystrophies, myopathies and myasthenias;

skin diseases, such as dermatitis, eczema, psoriasis, ageing, or also cicatrization changes;

cardiovascular diseases such as cardiac and/or vascular ischaemia, myocardial infarction, ischaemic cardiopathy, chronic or acute cardiac failure, cardiac dysrhythmia, atrial fibrillation, ventricular fibrillation, paroxystic tachycardia, cardiac failure, anoxia, hypoxia, side effects of therapies with anticancer agents;

circulatory diseases such as atherosclerosis, arteriosclerosis, peripheral vascular diseases, cerebral vascular accidents, aneurysms;

haematological and vascular diseases such as: anaemia, vascular amyloidosis, haemorrhage, sickle-cell anaemia, erythrocyte fragmentation syndrome, neutropenia, leukopenia, medullary aplasia, pancytopenia, thrombocytopenia, haemophilia;

lung diseases including pneumonia, asthma; chronic obstructive lung diseases such as for example chronic bronchitis and emphysema;

diseases of the gastro-intestinal tract, such as ulcers;

liver diseases including viral hepatitis and cirrhosis, liver diseases caused by toxins or medicaments, conditions which can lead to cirrhosis such as non-alcoholic steatohepatitis (NASH), Wilson's disease, primitive sclerosing cholangitis, or primitive biliary cirrhosis;

diseases of the pancreas such as for example acute or chronic pancreatitis;

metabolic diseases such as diabetes mellitus and insipidus, thyroiditis;

kidney diseases such as for example acute renal disorders or glomerulonephritis;

viral and bacterial infections such as septicaemia;

severe intoxications with chemical agents, toxins or medicaments;

degenerative conditions associated with Acquired Immune Deficiency Syndrome (AIDS);

disorders associated with ageing, such as accelerated ageing syndrome;

inflammatory diseases, such as Crohn's disease, rheumatoid arthritis;

auto-immune diseases such as lupus erythematosus;

dental disorders such as those leading to degradation of the tissues such as for example periodontitis;

opthalmic diseases or disorders including diabetic retinopathies, glaucoma, macular degenerations, retinal degeneration, retinitis pigmentosa, retinal holes or tears, detached retina, retinal ischaemia, acute retinopathies associated with trauma, inflammatory degenerations, post-surgery complications, drug-induced retinopathy, cataract;

disorders of the auditory pathways, such as otosclerosis and antibiotic-induced deafness;

diseases associated with mitochondria (mitochondrial pathologies), such as Friedrich's ataxia, congenital muscular dystrophy with structural mitochondrial anomalies, certain myopathies (MELAS syndrome, MERFF syndrome, Pearson syndrome), MIDD syndrome (maternally inherited diabetes and deafness), Wolfram syndrome, dystonia.

Very particularly, the medicaments according to the present invention are used because of their neuroprotective properties in the treatment or prevention of neurodegenerative conditions, such as for example Huntington's disease, chronic neurodegenerative diseases, advantageously chronic demyelinating diseases, hereditary or sporadic, neuronal lesions linked with ageing, neuropathies which are peripheral, hereditary or resulting from a lesion, neuropathies which are diabetic or caused by anticancer treatments, traumas of the brain, the peripheral nerves or the spinal cord, ischaemias of the brain or the spinal cord, epilepsy, degenerations which are hereditary, resulting from a lesion or linked with ageing of the sensory neurons of vision or degenerations of the optic nerve, degenerations which are hereditary, traumatic or linked with ageing of the sensory neurons of hearing, lobar atrophies and vascular dementias, and in particular spinal amyotrophies, amyotrophic lateral sclerosis and pathologies caused by traumas of the spinal cord or the peripheral motor nerves.

They are used in particular because of their neuroprotective properties vis-à-vis motor neurons, particularly in the treatment of spinal amyotrophies, in particular of amyotrophic lateral sclerosis or infantile spinal amyotrophies, and in the treatment of traumas of the spinal cord or the peripheral motor nerves as mentioned above.

In general the daily dose of the compound is the minimum dose for obtaining the therapeutic effect. This dose will depend on the different factors mentioned previously. The doses of the compounds described above, including 3-oxyimino-4-chloro-cholest-4-ene, 3-oxyimino-4-bromo-cholest-4-ene, 3-oxyimino-6-ethoxy-cholest-4,6-diene and 3-oxyimino-4-methyl-cholest-4-ene can in general be comprised between 0.001 and 100 mg per kilo, per day, for humans.

If necessary, the daily dose can be administered in two, three, four, five, six or more administrations per day, or by multiple sub-doses administered at appropriate intervals during the day.

The quantity chosen will depend on many factors, in particular the administration route, the duration of administration, the time of administration, the rate of elimination of the compound, the different product or products used in combination with the compound, the age, weight and physical condition of the patient, as well as their medical history, and any other known medical information.

The prescription of the attending physician can start at doses lower than those generally used, then these doses will be progressively increased in order to better control the appearance of possible side effects.

A subject of the invention is also the pharmaceutical compositions which include at least one compound of formula (I), including 3-oxyimino-4-chloro-cholest-4-ene, 3-oxyimino-4-bromo-cholest-4-ene, 3-oxyimino-6-ethoxy-cholest-4,6-diene and 3-oxyimino-4-methyl-cholest-4-ene or one of its esters and/or its addition salts with pharmaceutically acceptable acids, as active ingredient.

In these compositions, the active ingredient is advantageously present in physiologically effective doses; the abovementioned compositions can comprise in particular an effective neuroprotective dose of at least one abovementioned active ingredient.

As medicaments, the compounds corresponding to formula (I), including 3-oxyimino-4-chloro-cholest-4-ene, 3-oxyimino-4-bromo-cholest-4-ene, 3-oxyimino-6-ethoxy-cholest-4,6-diene. and 3-oxyimino-4-methyl-cholest-4-ene as well as their esters and/or their addition salts with pharmaceutically acceptable acids can be incorporated in pharmaceutical compositions intended for the digestive or parenteral route.

The pharmaceutical compositions according to the invention can also comprise at least one other therapeutically active ingredient, for simultaneous or separate use or use spread over time, in particular during treatment of a subject suffering from a pathology or trauma linked with the degeneration or death of cells, particularly of cardiac cells and/or motor neurons as defined above.

The pharmaceutical compositions or medicaments according to the invention advantageously comprise one or more inert, i.e. pharmaceutically inactive and non-toxic, excipients or vehicles. For example, saline, physiological, isotonic, buffered solutions, etc. can be mentioned, which are compatible with a pharmaceutical use and known to a person skilled in the art. The compositions can contain one or more agents or vehicles chosen from dispersants, solubilizers, stabilizers, preservatives, etc. Agents or vehicles which can be used in (liquid and/or injectable and/or solid) formulations are in particular methylcellulose, hydroxymethylcellulose, carboxymethylcellulose, cyclodextrins, polysorbate 80, mannitol, gelatin, lactose, vegetable or animal oils, acacia, etc. The compositions can be formulated in the form of an injectable suspension, gels, oils, tablets, suppositories, powders, gelatin capsules, capsules, etc., optionally using galenic forms or devices ensuring sustained and/or controlled release. For this type of formulation, an agent such as cellulose, carbonates or starches are advantageously used.

Administration can be carried out by any method known to a person skilled in the art, preferably by oral route or by injection, typically by intra-peritoneal, intracerebral, intrathecal, intravenous, intra-arterial or intramuscular route. Administration by oral route is preferred. With regard to long-term treatment, the preferred administration route is sublingual, oral or transcutaneous.

For injections, the compounds are generally packaged in the form of liquid suspensions, which can be injected using syringes or infusions, for example. It is understood that the flow rate and/or the dose injected, or the dose to be administered generally, can be adapted by a person skilled in the art depending on the patient, the pathology, the administration method, etc. It is understood that repeated administrations can be carried out, optionally in combination with other active ingredients or any pharmaceutically acceptable vehicle (buffers, saline, isotonic, solutions in the presence of stabilizers, etc.).

The invention can be used in mammals, in particular in humans.

A subject of the present invention is also a method for preparing a composition described above, characterized in that, according to methods known per se, the active ingredient or ingredients is/are mixed with acceptable, in particular pharmaceutically acceptable, excipients.

A particular subject of the invention is the use of a compound of formula (I) above, including 3-oxyimino-4-chloro-cholest-4-ene, 3-oxyimino-4-bromo-cholest-4-ene, 3-oxyimino-6-ethoxy-cholest-4,6-diene and 3-oxyimino-4-methyl-cholest-4-ene in the preparation of a medicament intended for the treatment or prevention of the pathologies or traumas linked to the degeneration or death of cells, particularly of cardiac cells and/or neurons, whether natural or accidental.

A more particular subject of the invention is also the use of a compound of formula (I) above, 3-oxyimino-4-chloro-cholest-4-ene, 3-oxyimino-4-bromo-cholest-4-ene, 3-oxyimino-6-ethoxy-cholest-4,6-diene and 3-oxyimino-4-methyl-cholest-4-ene in the preparation of a medicament intended for the treatment or prevention of necrosis and/or of pathological apoptosis and/or of necroptosis (antinecrotic and/or antiapoptotic and/or antinecroptotic medicaments) or also for the treatment or prevention of conditions such as:

diseases of the bones, joints, connective tissue and cartilage, such as osteoporosis, osteomyelitis, arthritis including for example osteoarthritis, rheumatoid arthritis and psoriatic arthritis, avascular necrosis, progressive ossifying fibrodysplasia, rickets, Cushing's syndrome;

muscle diseases such as muscular dystrophy, such as for example Duchenne's muscular dystrophy, myotonic dystrophies, myopathies and myasthenias;

skin diseases, such as dermatitis, eczema, psoriasis, ageing, or also cicatrization changes;

cardiovascular diseases such as cardiac and/or vascular ischaemia, myocardial infarction, ischaemic cardiopathy, chronic or acute cardiac failure, cardiac dysrhythmia, atrial fibrillation, ventricular fibrillation, paroxystic tachycardia, cardiac failure, anoxia, hypoxia, side effects of therapies with anticancer agents;

circulatory diseases such as atherosclerosis, arteriosclerosis, and peripheral vascular diseases, cerebral vascular accidents, aneurysms;

haematological and vascular diseases such as: anaemia, vascular amyloidosis, haemorrhage, sickle-cell anaemia, erythrocyte fragmentation syndrome, neutropenia, leukopenia, medullary aplasia, pancytopenia, thrombocytopenia, haemophilia;

lung diseases including pneumonia, asthma; chronic obstructive lung diseases such as for example chronic bronchitis and emphysema;

diseases of the gastro-intestinal tract, such as ulcers;

liver diseases including viral hepatitis and cirrhosis, liver diseases caused by toxins or medicaments, conditions which can lead to cirrhosis such as non-alcoholic steatohepatitis (NASH), Wilson's disease, primitive sclerosing cholangitis, or primitive biliary cirrhosis diseases of the pancreas such as for example acute or chronic pancreatitis;

metabolic diseases such as diabetes mellitus and insipidus, thyroiditis;

kidney diseases such as for example acute renal disorders or glomerulonephritis;

viral and bacterial infections such as septicaemia;

severe intoxications with chemical agents, toxins or medicaments;

degenerative conditions associated with Acquired Immune Deficiency Syndrome (AIDS);

disorders associated with ageing, such as accelerated ageing syndrome;

inflammatory diseases, such as Crohn's disease, rheumatoid arthritis;

auto-immune diseases such as lupus erythematosus;

dental disorders such as those leading to degradation of the tissues such as for example periodontitis;

opthalmic diseases or disorders including diabetic retinopathies, glaucoma, macular degenerations, retinal degeneration, retinitis pigmentosa, retinal holes or tears, detached retina, retinal ischaemia, acute retinopathies associated with trauma, inflammatory degenerations, post-surgery complications, drug-induced retinopathy, cataract;

disorders of the auditory pathways, such as otosclerosis and antibiotic-induced deafness;

diseases associated with mitochondria (mitochondrial pathologies), such as Friedrich's ataxia, congenital muscular dystrophy with structural mitochondrial anomalies, certain myopathies (MELAS syndrome, MERFF syndrome, Pearson syndrome), MIDD syndrome (maternally inherited diabetes and deafness), Wolfram syndrome, dystonia, and particularly neurodegenerative diseases such as for example Huntington's disease, chronic neurodegenerative diseases, advantageously chronic demyelinating and neurodegenerative diseases, hereditary or sporadic, in particular multiple sclerosis and leukodystrophies, neuronal lesions linked with ageing, peripheral neuropathies which are hereditary or resulting from a lesion, Charcot-Marie-Tooth disease, diabetic neuropathies or neuropathies induced by anti-cancer treatments, epilepsy, traumas of the brain, the peripheral nerves or the spinal cord, ischaemias of the brain or the spinal cord, degenerations which are hereditary, resulting from a lesion or linked with ageing of the sensory neurons of vision or degenerations of the optic nerve, degenerations which are hereditary, traumatic or linked with ageing of the sensory neurons of hearing, lobar atrophies and vascular dementias, the diseases and traumas linked to the degeneration of the motor neurons and more particularly spinal amyotrophies, particularly infantile, amyotrophic lateral sclerosis, multiple sclerosis and traumas of the spinal cord or the peripheral motor nerves.

A quite particular subject of the invention is the use of a compound of formula (I), including 3-oxyimino-4-chloro-cholest-4-ene, 3-oxyimino-4-bromo-cholest-4-ene, 3-oxyimino-6-ethoxy-cholest-4,6-diene and 3-oxyimino-4-methyl-cholest-4-ene in the preparation of a medicament intended for the treatment of spinal amyotrophies, particularly infantile, and amyotrophic lateral scleroses.

The use of these medicaments normally comprises the administration to patients, particularly to mammals, quite particularly to humans, of a therapeutically effective quantity of a compound of formula I, including 3-oxyimino-4-chloro-cholest-4-ene, 3-oxyimino-4-bromo-cholest-4-ene, 3-oxyimino-6-ethoxy-cholest-4,6-diene and 3-oxyimino-4-methyl-cholest-4-ene, in particular in order to increase the survival of cells, particularly of cardiac cells and/or neurons or to promote axonal growth.

A subject of the invention is equally a method for treating the abovementioned, in particular neurodegenerative, diseases and in particular a method for treating pathologies or traumas linked to the degeneration or death of neurons, in mammals (in general patients) suffering from such pathologies or traumas, comprising the administration to these mammals of a therapeutically effective quantity of a compound of formula I, including 3-oxyimino-4-chloro-cholest-4-ene, 3-oxyimino-4-bromo-cholest-4-ene, 3-oxyimino-6-ethoxy-cholest-4,6-diene and 3-oxyimino-4-methyl-cholest-4-ene in particular in order to increase the survival of neurons or to promote axonal growth.

A further subject of the invention is a method for treating one of the conditions described above and in particular pathologies or traumas linked to the degeneration or death of motor neurons, in mammals (in general patients) suffering from such pathologies or traumas, comprising the administration to these mammals of a therapeutically effective quantity of a compound of formula I, including 3-oxyimino-4-chloro-cholest-4-ene, 3-oxyimino-4-bromo-cholest-4-ene, 3-oxyimino-6-ethoxy-cholest-4,6-diene and 3-oxyimino-4-methyl-cholest-4-ene in particular in order to increase the survival of the neurons. More specifically, the pathologies linked to the degeneration or death of motor neurons are amyotrophic lateral sclerosis or infantile spinal amyotrophies. According to another variant, the invention also relates to compounds comprising a labelling group which can be detected and/or visualized directly or indirectly by detection and/or visualization techniques known to a person skilled in the art such as the fluorescence microscopy technique or the technique taking advantage of the very strong affinity of the avidins (streptavidin or neutravidin) for biotin (Ka~$10^7$M).

The term "labelling" generally refers to an entity such as a radioactive isotope or a non-isotopic entity such as a fluorophore agent, a colorant, a hapten, biotin, etc.

The term fluorophore refers in general to the feature of a substance being fluorescent, i.e. absorbing light energy (excitation light) when it is excited by an energy source and restoring it rapidly in the form of fluorescent light (emission light). This feature of being a fluorophore makes it possible to envisage the use of such a substance as a fluorescent label in biological systems (membranes, cells, neurons, mitochondria, etc) in order to carry out for example the imaging of the cells studied.

Biotin is a coenzyme, also called Vitamin H, synthesized by plants, bacteria and certain fungi. Biotin is detected by means of avidins (streptavidin or neutravidin) which have a very strong affinity for biotin (Ka~$10^7$M). The structure of biotin is as follows:

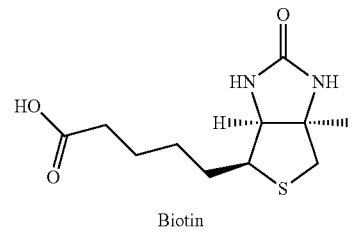 [SMILES: C[C@]12CS[C@@H](CCCCC(=O)O)[C@H]1NC(=O)N2]

Biotin

It is known in the prior art that the incorporation of a biotin group in a biologically active substance makes it possible to isolate and/or identify the protein targets or other non-protein compounds capable of interacting with said active substance using one of the approaches taking advantage of the very strong affinity of the avidins for biotin. The protein targets or other non-protein compounds thus isolated are for example characterized by mass spectrometry. Among the uses known to a person skilled in the art the following may be mentioned for example: diagnostic tests using biotinylated compounds; the ELISA test (Enzyme-Linked Immunosorbent Assay) which uses biotinylated antibiotics; affinity chromatography based on the use of an immobilized avidin column loaded with biotinylated compounds; the proteomic analysis technique (2D electrophoresis and mass spectrometry), etc.

The labelling group according to the present invention can be chosen from biotin or a fluorophore group such as 7-nitrobenz-2-oxa-1,3-diazol-4-yl (formula D); BODIPY® fluorophore; anthracene and fluorescein. Preferably, the labelling group according to the present invention is chosen from biotin and the 7-nitrobenz-2-oxa-1,3-diazol-4-yl fluorophore group (formula D).

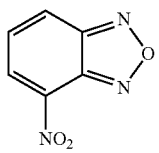

(D)

The compounds according to the present invention labelled with biotin or with a fluorophore group are probes which are very useful for:
- visualizing and/or detecting the cells which are in contact with the labelled compounds,
- studying their distribution in a living organism, human or animal, and their location in the cellular compartments (membranes, cells, neurons, mitochondria, nucleus, endoplasmic reticulum, golgi, lysosomes, endosomes and other organelles, etc),
- implementing a method for the detection of proteins or other non-protein compounds capable of interacting with said labelled compounds
- identifying their molecular target(s),
- studying the molecules-protein interactions from a molecular point of view,
- detecting the monoclonal antibodies specific to cholest-4-en-3-one oxime or its derivatives,
- developing and carrying out binding tests allowing, inter alia, the optimization of ligands with greater affinity for the target in question,
- developing assay methods,
- developing new ligand screening tools The incorporation of such a labelling group has not caused any loss in biological activity of the labelled compounds according to the present invention and has made possible the use of these labelled compounds as probes in particular as tracers or labelling agents.

As a result, another objective according to the invention is to provide compounds of formula (I) comprising a labelling group chosen from the NBD group and biotin.

A further subject of the invention is the use as probes, in particular as tracers or labelling agents, of the compounds of formula I, for which:

$R_6$ can represent a group corresponding to formula (A) below:

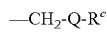  (A)

in which

Q can represent an oxygen atom or an $NR^a$ group, $R^a$ is as described previously, and $R^c$ can represent a group corresponding to formula (C) or (D)

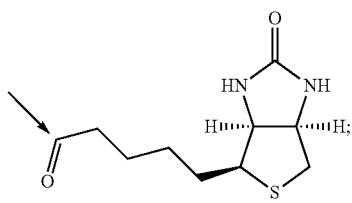  (C)

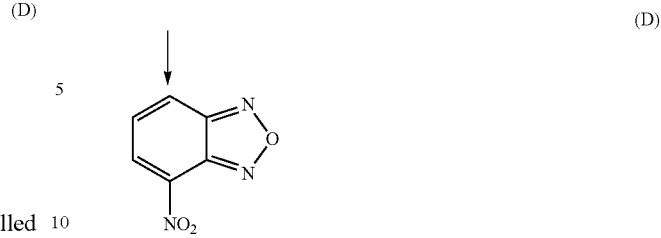  (D)

or, $R_{13}$ can represent a group corresponding to formula (E) below:

$$R_{14}-X-R_{15}$$  (E)

In which:

$R_{14}$ can represent the following $G_7$ group

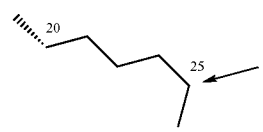  $G_7$

X can represent an oxygen atom, or $NR^a$, $R^a$ is as described previously, in particular NH or $NCH_3$, and $R_{15}$ can represent a group corresponding to formula (C) or (D) below

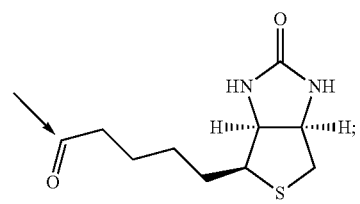  (C)

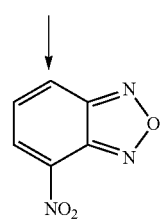  D

The compounds particularly preferred as tracers or labelling agents according to the invention are represented by formulae (III), (IV), (V) below:

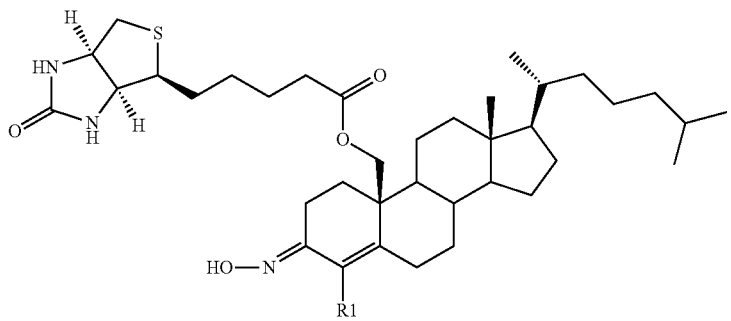

(III)

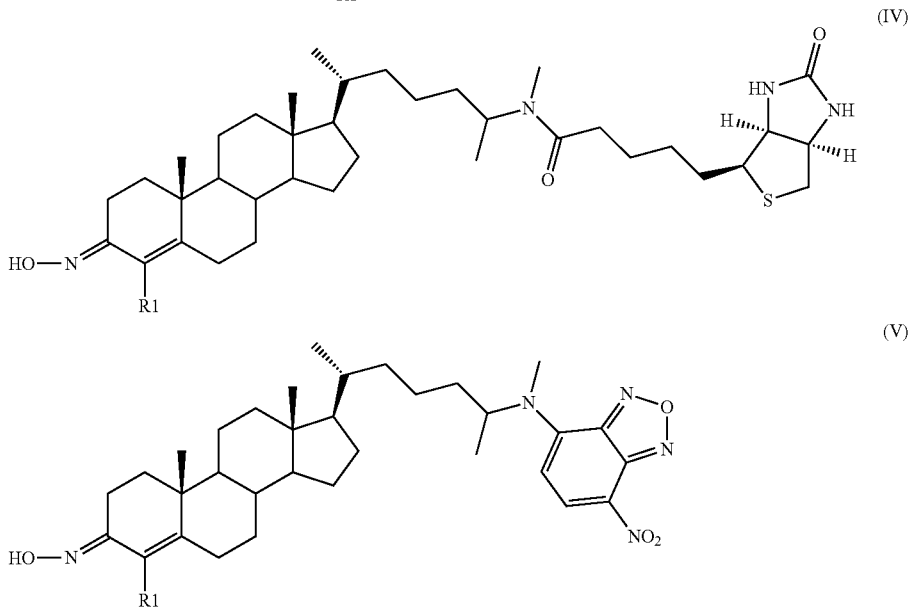

(IV)

(V)

formulae (III), (IV) or (V) in which the substituent $R_1$ can be as described previously. Preferentially, the substituent $R_1$ is a hydrogen atom.

The compounds of formula (I) according to the invention can be obtained by different synthesis methods using in particular the ketone oximation reaction which is well known to a person skilled in the art. The diagram below illustrates the method used for preparing the compounds of formula (I)

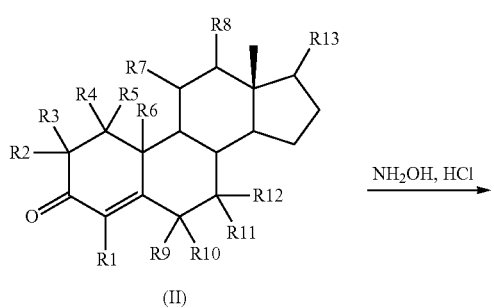

(II)

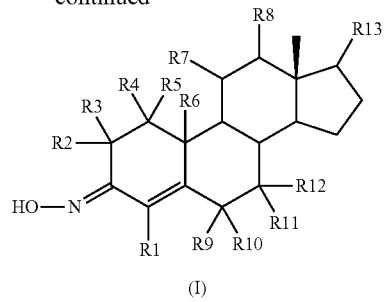

(I)

By way of example, a particularly appropriate method for obtaining the compounds of formula (I) consists of reacting:

(i) a compound of formula (II) in which the $R_1$ to $R_{13}$ groups are as defined previously, with (ii) a hydroxylamine halide such as hydroxylamine hydrochloride.

This method can advantageously be carried out in a suitable solvent such as pyridine.

The compounds of formula (I) can be isolated from the reaction medium by different methods well known to a person skilled in the art. Optionally, the compounds of formula (I) can be converted to one of their pharmaceutically acceptable salts. The compounds of formula (II) used as starting products for obtaining compounds of formulae (I)

are commercially available or are prepared by methods known to a person skilled in the art.

The following examples illustrate the present invention without however limiting it. The structures of the compounds described in the examples and in the preparations were determined according to the usual techniques (nuclear magnetic resonance, mass spectroscopy, etc).

ABBREVIATIONS

PE: petroleum ether
EA: ethyl acetate
s: singlet
d: doublet
t: triplet
sept: septuplet

EXAMPLE 1

Preparation of Compounds of Formula (II)

EXAMPLE 1a

Synthesis of 4-fluoro-cholest-4-en-3-one 4-fluoro-cholest-4-en-3-one was prepared according to the method described in the following articles: Toyota, A. & al. Chemical & Pharmaceutical Bulletin (1994), 42 (3), 459-61; and Nakanishi, S. & al: Chemistry & Industry (London, United Kingdom) (1960), 1136-7.

EXAMPLE 1b

Synthesis of 6β-fluoro-cholest-4-en-3-one

6β-fluoro-cholest-4-en-3-one was prepared according to one of the methods described in the following articles: Thomas, M. G. et al. Journal of the Chemical Society, Perkin Transactions 1: Organic and Bio-Organic Chemistry (1999), (21), 3191-3198; Poss, A. J. et al. Tetrahedron Letters (1995), 36 (27), 4721-4; Edmunds, J. J. et al. Journal of the Chemical Society, Chemical Communications (1989), (13), 881-3. Salmond, W. G. et al. Ger. Offen. (1983), DE 3225747; Nakanishi, S. et al. Journal of the American Chemical Society (1959), 81 5259-60.

EXAMPLE 1c

Synthesis of 2,2-difluoro-cholest-4-en-3-one and 2,6-difluoro-cholest-4-en-3-one 10 g (26 mmol) of cholest-4-en-3-one in suspension is added to 260 mL of methanol in a flask followed by 17.4 g (27.2 mmol) of 1-fluoro-4-hydroxy-1,4-diazoniabicyclo[2,2,2]octane bis(tetrafluoroborate) at 50% by mass on alumina. The medium is stirred at reflux for 16 hours and 7.7 g of the fluorination reagent is added; stirring is continued for 5 hours at reflux and for 4 days at ambient temperature. The reaction medium is then concentrated under vacuum and the residue is taken up in dichloromethane. After filtration, the solution obtained is concentrated under vacuum and the residue is taken up in 500 mL of 10% hydrochloric acid in acetonitrile. The suspension is stirred for 2 hours at ambient temperature and filtered. The precipitate is washed with ethyl acetate and the filtrate is extracted with ethyl acetate and the organic phase is concentrated under vacuum.

Purification of the precipitate by flash chromatography on silica gel (eluent PE/EA, gradient from 100% PE to 80/20 PE/EA) then by semi-preparative HPLC makes it possible to isolate 17.5 mg of 2,6-difluoro-cholest-4-en-3-one and 23.1 mg of 2,2-difluoro-4-cholesten-3-one.

The residue obtained from the filtrate is purified by flash chromatography on silica gel (eluent PE/EA, gradient from 100% PE to 80/20 PE/EA) then by semi-preparative HPLC makes it possible to isolate another 82 mg of 2,2-difluoro-cholest-4-en-3-one.

2,6-difluoro-cholest-4-en-3-one
$^1$H NMR (CDCl$_3$): δ (ppm) 6.11 (d, 1H, 4-CH), 5.21 (dddd, 1H, 2-CH), 4.86 (ddd, 1H, 6-CH), 0.71 (s, 3H, 18-CH$_3$).
LC/UV/MS (254 nm): T$_R$=5.82 min, m/z=421 [M+H]$^+$ 2,2-difluoro-cholest-4-en-3-one
$^1$H NMR (CDCl$_3$): δ (ppm) 6.26 (d, 1H, 4-OH), 0.73 (s, 3H, 18-CH$_3$)
NMR (CDCl$_3$): δ (ppm, non-calibrated) −86.33 (ddd, 2-CF$_a$), −101.04 (d, 2-CF$_b$)
LC/UV/MS (254 nm): T$_R$=6.48 min, m/z=421 [M+H]$^+$ EXAMPLE 1d Synthesis of 2α-fluoro-cholest-4-en-3-one 5 g (13 mmol) of cholest-4-en-3-one in suspension is added to 130 mL of methanol in a flask followed by 8.7 g (13.6 mmol) 1-fluoro-4-hydroxy-1,4-diazoniabicyclo[2,2,2]octane bis(tetrafluoroborate) at 50% by mass on alumina. The medium is stirred, at reflux for 3 hours and 4.3 g of the fluorination reagent is added; stirring is continued for 3 hours at reflux and overnight at ambient temperature. The reaction medium is then concentrated under vacuum and the residue is taken up in dichloromethane. After filtration, the solution obtained is concentrated under vacuum and the residue is taken up in 250 mL of 10% hydrochloric acid in acetonitrile. The suspension is stirred for 1 hour at ambient temperature and filtered. The precipitate is washed with ethyl acetate and the filtrate is extracted with ethyl acetate and the organic phase is concentrated under vacuum.

The residue obtained is purified by flash chromatography on silica gel (eluent PE/EA, gradient from 100% PE to 95/5 PE/EA) then semi-preparative HPLC makes it possible to isolate 30 mg of 2α-fluoro-cholest-4-en-3-one.

LC/UV/MS (254 nm): T$_R$=6.27 min (syn/anti), m/z=403 [M+H]$^+$

EXAMPLE 1e

Synthesis of 25-fluoro-cholest-4-en-3-one 100 mg (247 mmol) of 25-fluoro-5-cholesten-3β-ol and 15 mL of acetone are introduced into a flask at 0° C. then 160 μL of Jones reagent is added. The medium is stirred for 9 minutes at 0° C. then the reaction is stopped by adding ethanol. After concentration under vacuum at a temperature below 30° C., the residue is taken up in 10 mL of ethanol and 100 μL of a 1N hydrochloric acid solution is added. The medium is stirred for 15 minutes at 50-60° C. then concentrated under vacuum. The residue obtained is taken up in water and extracted with ethyl acetate; the organic phase is separated, washed with water, dried over anhydrous magnesium sulphate and concentrated under vacuum. After purification by flash chromatography on silica gel (petroleum ether then petroleum ether/ethyl acetate 95/5), 69 mg of the enone is obtained with a yield of 69%.

LC/UV/MS (254 nm): T$_R$=5.41 min, m/z=403 [M+H]$^+$

EXAMPLE 1f

Synthesis of 25-[methyl(7-nitro-2,1,3-benzoxadiazol-4-yl)amino]-27-norcholest-5-en-3-one, and 25-((N-(+)-biotinoyl-N-methyl)amino)-27-norcholest-4-en-3-one

Stage 1: Synthesis of tert-butyldimethylsilyl-25-(N-methylamino)-27-norcholesterol 2.83 g (5.65 mmol) of tert-butyldimethylsilyl-25-keto-27-norcholesterol[(1)], 3.62 g (53.67 mmol) of N-methylamine hydrochloride and 355 mg (5.65 mmol) of sodium cyanoborohydride in 40 mL of methanol are introduced into a flask. The solution is stirred overnight at ambient temperature then the medium is concentrated under vacuum. The residue is taken up in a 2M sodium carbonate solution in water and extracted 3 times with dichloromethane. The organic phases are combined, washed with a saturated sodium chloride solution, dried over anhydrous magnesium sulphate, filtered and concentrated under vacuum. The product obtained is used as it is without purification.

LC/DEDL/MS: $T_R$=10.42 min, m/z=516 [M+H]$^+$ $^1$H NMR (CDCl$_3$): δ (ppm) 5.29-5.33 (multiplet, 1H, 6-CH), 3.47 (m, 1H, 3-CH), 2.10-2.55 (multiplet, 4H, 25-CH and NCH$_3$), 0.67 (s, 3H, 18-CH$_3$), 0.05 (s, 6H, Si (CH$_3$)$_2$)

(1) Ferraboschi, P. et al., *Tetrahedron Asymmetry* (1999), 10 (13), 2497-2500; Ferraboschi, P. et al., *Tetrahedron: Asymmetry* (1998), 9 (13), 2193-2196. Okamoto, M. et al. *Jpn. Kokai Tokkyo Koho* (1997), 15 pp. CODEN: JKXXAF JP 09249691 A 19970922; Satsangi, R. K. et al. Analyst (Cambridge, United Kingdom) (1992), 117 (6), 953-7.

Stage 2: Synthesis of 25-(N-methylamino)-27-norcholesterol 2 g (3.87 mmol) of tert-butyldimethylsilyl-25-(N-methylamino)-27-norcholesterol obtained in stage 1 in 12 mL of dichloromethane are introduced into a flask. 4 mL of a 4N hydrogen chloride solution in dioxane is added dropwise. The reaction medium is stirred for 1 hour at ambient temperature then filtered on frit. The filtrate is basified by adding a soda solution and extracted 3 times with dichloromethane. The organic phases are combined, dried over anhydrous magnesium sulphate, filtered and concentrated under vacuum. The product obtained is used as it is without purification.

LC/DEDL/MS: $T_R$=1.85 and 2.08 min, m/z=402 [M+H]$^+$ $^1$H NMR (CDCl$_3$): δ (ppm) 5.29-5.40 (multiplet, 1H, 6-CH), 3.50 (m, 1H, 3-CH), 2.10-2.65 (multiplet, 4H, 25-CH and NCH$_3$), 0.67 (s, 3H, 18-CH$_3$).

Stage 3: Synthesis of 25-(N-methylamino)-27-norcholest-4-en-3-one 870 mg (2.16 mmol) of 25-(N-methylamino)-27-norcholesterol obtained in stage 1, 15 mL of acetone and 6 mL of dichloromethane are introduced into a flask at 0° C. then 1.1 mL of Jones reagent is added. The medium is stirred for 20 minutes at 0° C. then the reaction is stopped by adding 2 mL of ethanol. After concentration under vacuum at a temperature below 30° C., the residue is taken up in 15 mL of ethanol and 725 μL of a 1N hydrochloric acid solution is added. The medium is stirred for 20 minutes at 50° C. then concentrated under vacuum. The residue obtained is taken up in water and extracted 3 times with dichloromethane; the organic phases are combined, washed with a saturated sodium chloride solution, dried over anhydrous magnesium sulphate and concentrated under vacuum. After purification by flash chromatography on silica gel (dichloromethane/methanol, gradient 95/5 to 8/2), 106 mg of the enone is obtained with a yield of 12%.

LC/UV/MS (254 nm): $T_R$=7.35 min, m/z=400 [M+H]$^+$ $^1$H NMR (CDCl$_3$): δ (ppm) 5.72 (s, 1H, 4-CH), 2.86 (m, 1H, 25-CH), 2.10-2.60 multiplet, 3H, NCH$_3$), 0.70 (s, 3H, 18-CH$_3$).

Stage 4: Synthesis of 25-[methyl(7-nitro-2,1,3-benzoxadiazol-4-yl)amino]-27-norcholest-5-en-3-one 106 mg (0.265 mmol) of 25-(N-methylamino)-27-norcholest-4-en-3-one obtained in stage 3, 58.3 mg (0.292 mmol) of 4-chloro-7-nitrobenzofurazane and 74 μL of triethylamine in 8 mL of dichloromethane are introduced into a flask. The solution is stirred overnight at ambient temperature protected from light then the reaction medium is diluted in dichloromethane. The solution obtained is washed with a 1N hydrochloric acid solution (3 times), dried over anhydrous magnesium sulphate and concentrated under vacuum. The residue obtained is purified by flash chromatography on silica gel (eluent dichloromethane/ethyl acetate 95/5) then by reversed-phase flash chromatography (eluent acetonitrile). 27 mg of the expected product is obtained in the form of brown solid (yield 18%).

LC/UV/MS (254 nm): $T_R$=4.75 min, m/z=563 [M+H]$^+$ $^1$H NMR (CDCl$_3$): δ (ppm) 8.44 (d, 1H, NBD-CH), 6.16 (d, 1H, NBD-CH), 5.71 (s, 1H, 4-CH), 2.93-3.25 (multiplet, 4H, 25-CH and NCH$_3$), 0.66 (d, 3H, 18-CH$_3$).

Stage 4': Synthesis of 25-((N-(+)-biotinoyl-N-methyl)amino)-27-norcholest-4-en-3-one 82 mg (0.205 mmol) of 25-(N-methylamino)-27-norcholest-4-en-3-one obtained in stage 3, 43 mg (0.226 mmol) of 1-(3-dimethylaminopropyl)-3-ethylcarboiimide, 33 mg (0.267 mmol) of N,N-dimethylaminopyridine and 55 mg (0.226 mmol) of D (+)-biotin in 2 mL of N,N-dimethylformamide and 1 mL of dichloromethane are introduced into a flask. The reaction medium is stirred overnight at ambient temperature then it is immersed in water and extracted 3 times with dichloromethane. The organic phases are combined, washed with a saturated sodium chloride solution, dried over anhydrous magnesium sulphate and concentrated under vacuum. After purification by flash chromatography on silica gel (gradient 100% dichloromethane to 95/5 dichloromethane/methanol), 90 mg of the amide is obtained with a yield of 70%.

LC/UV/MS (254 nm): $T_R$=9.14 min, m/z=626 [M+H]$^+$

EXAMPLE 1g

Synthesis of 19-biotinyloxy-cholest-4-en-3-one 112 mg (0.582 mmol) of 1-(3-dimethylaminopropyl)-3-ethylcarboiimide, 84 mg (0.688 mmol) of N,N-dimethylaminopyridine and 142 mg (0.582 mmol) of D (+)-biotin in 3.5 mL of N,N-dimethylformamide and 2 mL of dichloromethane are introduced into a flask. The medium is stirred for 45 minutes at ambient temperature then 212 mg (0.529 mmol) of 19-hydroxy-cholest-4-en-3-one* in solution in 2 mL of N,N-dimethylformamide are added dropwise. The medium is stirred for 48 hours at ambient temperature then it is concentrated under vacuum. The residue is taken up in water and extracted 3 times with ethyl acetate. The organic phases are combined, washed with a saturated sodium chloride solution, dried over anhydrous magnesium sulphate and concentrated under vacuum. After purification by flash chromatography on silica gel (gradient 100% dichloromethane to 95/5 dichloromethane/methanol), 180 mg of the 19-biotinyloxy-cholest-4-en-3-one ester is obtained with a yield of 54%.

* the compound 19-hydroxy-cholest-4-en-3-one is commercially available.

$^1$H NMR (CDCl$_3$): δ (ppm) 5.91 (s, 1H), 4.72 (d, 1H), 4.52 (m, 1H), 4.32 (m, 1H), 4.12 (d, 1H), 3.13 (m, 1H), 2.93 (dd, 1H), 0.70 (s, 3H)

LC/UV/MS (254 nm): T$_R$=4.85 min, m/z=627 [M+H]$^+$

EXAMPLE 1h

Synthesis of 2-methyl-cholest-4-en-3-one 2-methyl-cholest-4-en-3-one was prepared according to the method described in the following article: Julia, S. & al. Journal of Chemical Society (1964), August, 2633-9.

EXAMPLE 1i

Synthesis of 4-methoxy-cholest-4-en-3-one 4-methoxy-cholest-4-en-3-one was prepared according to the method described in the following articles: Patel, K. M. & al. Journal of Organic Chemistry (1975), 40 (10), 1504-5 and Engelfried, O. & al Patent DE 1117112 (1961).

EXAMPLE 2

Synthesis of Compounds of Formula (I)

EXAMPLE 2a

General Method A

One equivalent of ketone and six equivalents of hydroxylamine hydrochloride in pyridine (approximately 10 to 20 mL/mmol) are introduced into a flask. The solution is stirred overnight at ambient temperature then the reaction medium is concentrated under vacuum. The residue obtained is taken up in water and extracted with dichloromethane or ethyl acetate; the organic phase is separated, washed with water, dried over anhydrous magnesium sulphate and concentrated under vacuum. If necessary the product is purified by flash chromatography on silica gel.

EXAMPLE 2b

Synthesis of 3-oxyimino-4-fluoro-cholest-4-ene 3-oxyimino-4-fluoro-cholest-4-ene is obtained from the 4-fluoro-cholest-4-en-3-one prepared in Example 1a, with a quantitative yield according to method A.

$^1$H NMR (CDCl$_3$): δ (ppm) 3.02 (dd, 2H, 2-CH$_2$), 2.23 (td, 1H, 6-CH$_a$) 0.69 (3H, 18-CH$_3$).

NMR (CDCl$_3$): δ (ppm, non-calibrated) −137.35 (s, 4-CF)

LC/UV/MS (254 nm): T$_R$=6.42 min, m/z=418 [M+H]$^+$

EXAMPLE 2c

Synthesis of 3-oxyimino-6β-fluoro-cholest-4-ene 3-oxyimino-6β-fluoro-cholest-4-ene is obtained in the form of syn/anti mixture from the 6β-fluoro-cholest-4-en-3-one prepared in Example 1b, with a yield of 93% according to method A.

$^1$H NMR (CDCl$_3$): δ (ppm) 6.75 (d, 0.3H, 4-CH [syn]), 6.07 (d, 0.7H, 4-CH [anti]), 5.01 (dt, 0.3H, 6-CH [syn]), 4.97 (dt, 0.7H, 6-CH [anti]), 3.07 (d, 0.7H, 2-CH$_a$ [anti]), 0.72 (s, 3H, 18-CH$_3$).

NMR (CDCl$_3$): δ (ppm, non-calibrated) −159.23 (td, 6-CF [anti]), −162.05 (td, 6-CF [syn])

LC/UV/MS (254 nm) T$_R$=5.88 and 5.96 min (syn/anti), m/z=418 [M+H]$^+$

EXAMPLE 2d

Synthesis of 3-oxyimino-2,2-difluoro-cholest-4-ene 3-oxyimino-2,2-difluoro-cholest-4-ene is obtained in the form of syn/anti mixture from the 2,2-difluoro-4-cholesten-3-one prepared in Example 1c, with a yield of 89% according to method A.

$^1$H NMR (CDCl$_3$): δ (ppm) 7.18 (d, 0.3H, 4-CH [syn]), 6.49 (d, 0.7H, 4-CH [anti]), 3.09 (broad d, 0.7H), 0.71 (s, 3H, 18-CH$_3$).

LC/UV/MS (254 nm): T$_R$=6.06 min, m/z=436 [M+H]$^+$

EXAMPLE 2e

Synthesis of 3-oxyimino-2,6-difluoro-cholest-4-ene 3-oxyimino-2,6-difluoro-cholest-4-ene is obtained in the form of syn/anti mixture from the 2,6-difluoro-cholest-4-en-3-one prepared in Example 1c, with a yield of 97% according to method A.

$^1$H NMR (CDCl$_3$): δ (ppm) 6.84 (s, 0.35H, 4-CH [syn]), 6.25 (s, 0.65H, 4-CH [anti]), 5.94 (broad d, 1H, 2-CH), 5.13 (broad d, 1H, 6-CH), 0.70 (s, 3H, 18-CH$_3$).

$^{19}$F NMR (CDCl$_3$): δ (ppm, non-calibrated) −171.52 (td, 2-CF [syn]), −180.75 (td, 2-CF [anti]), −183.56 (d, 6-CF [syn]), −184.02 (d, 6-CF [anti]). LC/UV/MS (254 nm): T$_R$=5.68 min, m/z=436 [M+H]$^+$

EXAMPLE 2f

Synthesis of 3-oxyimino-2α-fluoro-cholest-4-ene 3-oxyimino-2α-fluoro-cholest-4-ene is obtained in the form of syn/anti mixture from the 2α-fluoro-cholest-4-en-3-one prepared in Example 1d, with a yield of 97% according to method A.

$^1$H NMR (CDCl$_3$): δ (ppm) 6.87 (s, 0.3H, 4-CH [syn]), 6.21 (s, 0.7H, 4-CH [anti]), 5.08 (ddd, 1H, 2-CH), 3.08 (broad d, 0.7H), 0.69 (s, 3H, 18-CH$_3$).

NMR (CDCl$_3$): δ (ppm, non-calibrated) −183.12 (ddd, 2-CF [syn]), −183.66 (ddd, 2-CF [anti])

LC/UV/MS (254 nm): T$_R$=5.78 and 5.99 min (syn/anti), m/z=418 [M+H]$^+$

EXAMPLE 2g

Synthesis of 3-oxyimino-25-fluoro-cholest-4-ene 3-oxyimino-25-fluoro-cholest-4-ene is obtained in the form of syn/anti mixture from the 25-fluoro-cholest-4-en-3-one prepared in Example 1e, with a yield of 83% according to method A.

$^1$H NMR (CDCl$_3$): δ (ppm) 6.46 (s, 0.4H, 4-CH [syn]), 5.77 (s, 0.6H, 4-CH [anti]), 3.04 (d, 0.6H, 2-CH, [anti]), 0.70 (s, 3H, 18-CH$_3$).

NMR (CDCl$_3$): δ (ppm, non-calibrated) −137.01 (sept, 25-CF).

LC/UV/MS (254 nm) $T_R$=4.44 and 4.84 min (syn/anti), m/z=418 [M+H]$^+$

EXAMPLE 2h

Synthesis of 3-oxyimino-25-[methyl(7-nitro-2,1,3-benzoxadiazol-4-yl)amino]-27-norcholest-4-ene 25 mg (0.044 mmol) of 25-[methyl(7-nitro-2,1,3-benzoxadiazol-4-yl)amino]-27-norcholest-4-en-3-one prepared in Example 1f stage 4, and 25 mg (0.36 mmol) of hydroxylamine hydrochloride in 2 mL of pyridine are introduced into a flask. The solution is stirred overnight at ambient temperature then the reaction medium is diluted in dichloromethane. The solution obtained is washed with water, dried over anhydrous magnesium sulphate and concentrated under vacuum. 26 mg of 3-oxyimino-25-[methyl (7-nitro-2,1,3-benzoxadiazol-4-yl)amino]-27-norcholest-4-ene are thus obtained in the form of an orange solid (yield 89%).

LC/UV/MS (254 nm): $T_R$=3.34, 3.64 and 3.95 min, m/z=578 [M+H]$^+$ $^1$H NMR (CDCl$_3$): δ (ppm) 8.45 (d, 1H, NBD-CH), 6.45 (s, 0.34H, 4-CH [syn]), 6.16 (d, 1H, NBD-CH), 5.80 (s, 0.66H, 4-CH [anti]), 2.94-3.30 (multiplet, 4H, 25-CH and NCH$_3$), 0.64 (d, 3H, 18-CH$_3$).

EXAMPLE 2i

Synthesis of 3-oxyimino-25-((N-(+)-biotinoyl-N-methyl)amino)-27-norcholest-4-ene 65 mg (0.104 mmol) of 25-((N-(+)-biotinoyl-N-methyl) amino)-27-norcholest-4-en-3-one prepared in Example 1f stage 4', and 65 mg (0.935 mmol) of hydroxylamine hydrochloride in 2 mL of pyridine are introduced into a flask. The solution is stirred overnight at ambient temperature then the pyridine is concentrated under vacuum. The residue is taken up in water and extracted 4 times with ethyl acetate. The organic phases are combined, washed with a saturated sodium chloride solution, dried over anhydrous magnesium sulphate and concentrated under vacuum. 66 mg of 3-oxyimino-25-((N-(+)-biotinoyl-N-methyl)amino)-27-norcholest-4-ene is thus obtained in the form of a beige solid (yield 98%).

LC/UV/MS (254 nm): $T_R$=8.56 and 8.81 min, m/z=641 [M+H]$^+$ $^1$H NMR (CDCl$_3$): δ (ppm) 6.46 (s, 0.3H, 4-CH [syn]), 5.77 (s, 0.7H, 4-CH [anti]), 2.68-2.81 (multiplet, 4H), 2.85-3.23 (multiplet, 3H), 3.82 (m, 0.5H), 4.33 (m, 1H), 4.51 (m, 1H), 4.73 (m, 0.5H), 4.90-5.01 (multiplet, 1H), 5.35-5.49 (multiplet, 1H), 0.68 (broad s, 3H, 18-CH$_3$).

EXAMPLE 2j 3-oxyimino-7α-hydroxy-cholest-4-ene 3-oxyimino-7α-hydroxy-cholest-4-ene is obtained in the form of syn/anti mixture from 7α-hydroxy-cholest-4-en-3-one* with a quantitative yield according to method A.

* 7α-hydroxy-4-cholesten-3-one is commercially available.

$^1$H NMR (CDCl$_3$): δ (ppm) 6.56 (s, 0.3H), 5.87 (s, 0.7H), 3.85-3.94 (multiplet, 1H), 3.92-4.08 (multiplet, 1H), 3.05 (dt, 0.7H), 2.56 (broad d, 1H), 1.07 (s, 3H), 0.90 (d, 3H), 0.86 (dd, 6H), 0.69 (s, 3H)

LC/UV/MS (254 nm): $T_R$=3.19 and 3.56 min (syn/anti), m/z=416 [M+H]$^+$

EXAMPLE 2k 3-oxyimino-19-hydroxy-cholest-4-ene 3-oxyimino-19-hydroxy-cholest-4-ene is obtained in the form of syn/anti mixture from 19-hydroxy-cholest-4-en-3-one* with a yield of 96% according to method A.

* 19-hydroxy-4-cholesten-3-one is commercially available.

$^1$H NMR (CDCl$_3$): δ (ppm) 6.75 (s, 0.25H), 6.07 (s, 0.75H), 3.69-3.81 (multiplet, 1H), 3.92-4.08 (multiplet, 1H), 2.96 (broad d, 1H), 0.68 (s, 3H)

LC/UV/MS (254 nm): $T_R$=3.81 and 4.27 min (syn/anti), m/z=416 [M+H]$^+$

EXAMPLE 2l 3-oxyimino-19-biotinyloxy-cholest-4-ene 3-oxyimino-19-biotinyloxy-cholest-4-ene is obtained in the form of syn/anti mixture from the 19-biotinyloxy-cholest-4-en-3-one ester prepared in Example 1 g, with a yield of 92% according to method A.

$^1$H NMR (CDCl$_3$): δ (ppm) 6.76 (s, 0.3H), 6.62 (broad s, 1H), 5.93 (s, 0.7H), 4.89 (d, 0.7H), 4.73 (d, 0.3H), 4.50 (m, 1H), 4.34 (m, 1H), 4.03 (d, 0.3H), 3.85 (d, 0.7H), 2.15-3.20 (multiplet, 8H), 0.69 (s, 3H)

LC/UV/MS (254 nm): $T_R$=4.41 and 4.55 min (syn/anti), m/z=642 [M+H]$^+$

EXAMPLE 2m

Synthesis of 3-oxyimino-2-methyl-cholest-4-ene 3-oxyimino-2-methyl-cholest-4-ene is obtained from the 2-methyl-cholest-4-en-3-one prepared in Example 1 h, with a quantitative yield according to method A.

$^1$H NMR (CDCl$_3$): δ (ppm) 6.44 (s, 0.7H), 5.78 (s, 0.20H), 0.70 (s, 3H)

LC/UV/MS (254 nm): $T_R$=6.42 and 6.74 min (syn/anti), m/z=414 [M+H]$^+$

EXAMPLE 2n

Synthesis of 3-oxyimino-4-methoxy-cholest-4-ene 3-oxyimino-4-methoxy-cholest-4-ene is obtained from the 4-methoxy-cholest-4-en-3-one prepared in Example 1l, with a quantitative yield according to method A.

$^1$H NMR (CDCl$_3$): δ (ppm) 3.57 (s, 3H), 3.03 (dd, 2H), 0.69 (s, 3H)

LC/UV/MS (254 nm): $T_R$=6.36 min, m/z=430 [M+H]$^+$

Pharmacological Study

The compounds were tested according to the following protocols:

Effects of the Compounds of Formulae (I) on the Survival of the Motor Neurons

In order to demonstrate the neuroprotective action of the compounds of formula e (I), the applicant studied their activity on an in vitro model of trophic deprivation of rat motor neurons. Reference can usefully be made to the applicant's patent application WO 0142784 on the culturing of motor neurons of the spinal cord.

The spinal cord of E14 rat embryos is dissected and the ventral part is dissociated by trituration after trypsination.

The motor neurons are separated from the other spinal cells by a known method (Camu et al., 1993, Purification of spinal motoneurons from chicken and rat embryos by immunopanning. In "Immunoselection Strategies for Neural cell culture", Neuroprotocols: A companion to Methods in Neurosciences 2, 191-199; Henderson et al., 1993, Neutrophins promote motor neuron survival and are present in embryonic limb bud. Nature 363 (6426):266-70).

The cells are centrifuged on a density gradient. The fraction of large cells (the least dense) is enriched with motor neurons. The cells in this fraction are incubated with an anti-p75 antibody, a surface antigen present on the motor neurons.

Secondary antibodies coupled to magnetic beads are added and the mixture of cells is passed through a column in a magnet (Arce et al., 1999 Cardiotrophin-1 requires LIFRbeta to promote survival of mouse motoneurons purified by a novel technique. J. Neurosci Res 55 (1): 119-26). Only the motor neurons are retained: their purity is of the order of 90%.

The motor neurons are seeded at a low density in culture wells on a polyornithine-laminin substrate in a neurobasal medium (GIBCO) supplemented according to Raoul et al., 1999, Programmed cell death of embryonic motoneurons triggered through the Fas death receptor. J Cell Biol 147 (5):1049-62.

Negative controls (absence of trophic factors) and positive controls (in the presence of BDNF (Brain-Derived Neurotrophic Factor) at 1 ng/ml, GDNF (Glial-Derived Neurotrophic Factor) at 1 ng/ml and CNTF (Ciliary Neurotrophic Factor) at 10 ng/ml, marketed by the American company PEPROTECH, Inc. and the company Sigma-Aldrich, are included in each series.

The compounds to be tested are added 60 minutes after seeding and the cultures are maintained at 37° C. under 5% $CO_2$ for 3 days.

The motor neurons have a spontaneous tendency to die in the absence of neurotrophic factors (Pettmann and Henderson, 1998, Neuronal cell death. Neuron 20 (4):633-47). After 3 days, the survival is evaluated by a fluorescence measurement after incubation of the cells in the presence of calcein which becomes fluorescent in living cells.

After 3 days in culture at 37° C., under 5% $CO_2$ and under saturation humidity, up to 50% of the motor neurons initially seeded survive in the medium supplemented with neurotrophic factors, whilst less than 15% of the motor neurons survive in culture medium without added neurotrophic factors.

The neuroprotective activity of the compounds to be tested was evaluated by their ability to prevent the death of the motor neurons when they are added to the Neurobasal medium (GIBCO) in comparison with the survival of the motor neurons in medium with added neurotrophic factors.

The compounds of formula I according to the invention exhibited a neuroprotective activity at a concentration capable of allowing a better survival rate of the motor neurons in the Neurobasal medium.

This survival rate is expressed by the number of living cells after treatment with the compound to be tested compared with the survival induced by the neurotrophic factors. This ratio can therefore represent the survival percentage due to the compound tested compared with the survival induced by the neurotrophic factors. If the ratio is greater than 0, the effect of the compounds on the survival of the motor neurons is positive.

The results obtained are as follows:

| Compound of Example | Concentration in μM | Ratio |
|---|---|---|
| 2b | 3 | 0.73 |
| 2c | 3 | 0.50 |
| 2d | 3 | 0.50 |
| 2e | 3 | 0.37 |
| 2f | 3 | 0.27 |
| 2h | 1 | 0.66 |
| 2i | 3 | 0.42 |
| 2k | 3 | 0.49 |
| 2l | 1 | 0.32 |
| 2m | 1 | 0.42 |
| 2n | 1 | 0.34 |

By virtue of their trophic effect on the spinal motor neurons, the compounds of formula (I) according to the invention therefore prove to be potentially useful as medicaments, in particular in the treatment of the amyotrophies, in particular in the treatment of amyotrophic lateral sclerosis or infantile spinal amyotrophies, and in the treatment of traumas of the spinal cord.

The invention claimed is:

1. A compound of formula I

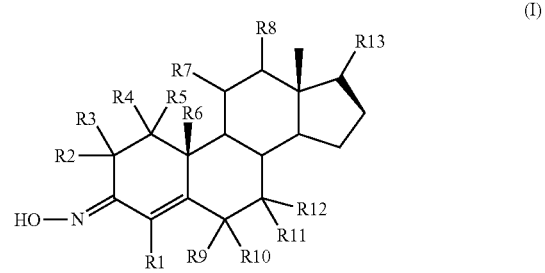

in which, when $R_1$ represents a hydrogen atom then $R_{13}$ represents (i) a linear or branched $C_4$-$C_{12}$ hydrocarbon radical, substituted once or several times by one of the substituents chosen independently from a halogen atom or a —CN, —CF3, COORa —CONRaRb, —O—, CONRaRb, —ORa, —SRb group, the Ra and Rb groups either (a) simultaneously or independently of each other, are chosen from a hydrogen atom or a $C_1$-$C_6$ alkyl, $C_3$-$C_6$ cycloalkyl, aryl, or heteroaryl group; or (b) together form a linear or branched hydrocarbon chain of 2 to 6 carbon atoms, optionally with one or more double bonds and/or optionally interrupted by one or more oxygen, sulphur or nitrogen atom(s)

(ii) a group corresponding to formula E below:

$$R_{14}—X—R_{15} \quad (E)$$

in which:

$R_{14}$ represents a $C_4$-$C_{12}$ alkyl group or a $C_4$-$C_{12}$ alkenyl group, X represents an oxygen atom or an —NRa group with Ra being chosen from a hydrogen atom or a $CH_3$, $C_3$-$C_6$ alkyl, $C_3$-$C_6$ cycloalkyl, aryl, heteroaryl group, and $R_{15}$ represents a $C_3$-$C_6$ cycloalkyl, aryl, heteroaryl group, a heterocycle, —C(O)—$C_1$-$C_6$ alkyl, —C(O)—$C_3$-$C_6$ cycloalkyl, —CO)-aryl, —C(O)-heteroaryl, or —C(O)-heterocycle: or when $R_1$ represents a $C_1$-$C_6$ alkyl, $C_3$-$C_6$ cycloalkyl, $C_2$-$C_6$ alkenyl, $C_2$-$C_6$ alkynyl, aryl group, a heterocycle, or a halogen atom or a —CN, —$CF_3$, —$NO_2$, —OR$^a$, —SR$^a$, —SO$_2$R$^a$, —NR$^a$R$^b$, —OC(O)R$^a$, —OC(O)NR$^a$R$^b$, —C(O)OR$^a$, —CONR$^a$R$^b$ group in which the Ra and Rb groups are as defined above, then R$_{13}$ represents (i) a linear or branched C$_4$-C$_{12}$ hydrocarbon radical, substituted once or several times by one of the substituents chosen independently from a halogen atom or a —CN, —CF3, COORa, —CONRaRb, —O—CON-RaRb, —ORa, —SRb group, the Ra and Rb groups being as defined above; or (ii) a C$_4$-C$_{12}$ alkenyl group, or a group chosen from

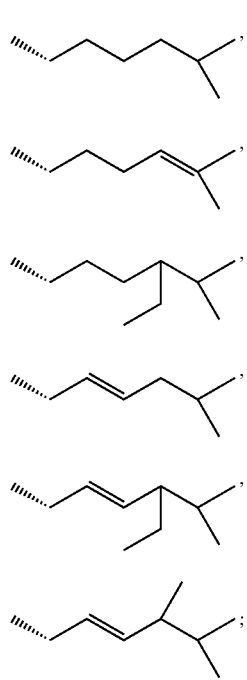

G$_1$

G$_2$

G$_3$

G$_4$

G$_5$

G$_6$ or (iii) a group corresponding to formula E below:

R$_{14}$—X—R$_{15}$ (E)

in which:
R$_{14}$ represents a C$_4$-C$_{12}$ alkyl group or a C$_4$-C$_{12}$ alkenyl group,
X represents an oxygen atom or an —NRa group with Ra being chosen from a hydrogen atom or a CH$_3$, C$_3$-C$_6$ alkyl, C$_3$-C$_6$ cycloalkyl, aryl, heteroaryl group, and
R$_{15}$ represents a C$_3$-C$_6$ cycloalkyl, aryl, heteroaryl group, a heterocycle, —C(O)—C$_1$-C$_6$ alkyl, —C(O)—C$_3$-C$_6$ cycloalkyl, —CO)-aryl, —C(O)-heteroaryl, or —C(O)-heterocycle:

R$_2$ represents a hydrogen atom, or a C$_1$-C$_6$ alkyl, C$_3$-C$_6$ cycloalkyl, aryl group or a halogen atom;

R$_3$ represents a hydrogen atom, or a C$_1$-C$_6$ alkyl group or a halogen atom or a —CN, —OR$^a$, —SR$^a$, —SeR$^a$, —COOR$^a$, —NR$^a$R$^b$, —OCONR$^a$R$^b$ group, —R$^a$ and —R$^b$ being as defined above; or R$_3$ and R$_2$ together with the carbon to which they are attached, form a (C$_3$-C$_6$)-cycloakyl group;

R$_4$ represents a hydrogen atom or a C$_1$-C$_6$ alkyl group; or

R$_4$ and R$_2$ together form an additional carbon-carbon bond between the carbon atoms to which R$_2$ and R$_4$ are attached, or a C$_3$-C$_6$ cycloalkyl group;

R$_5$ represents a hydrogen atom or an —OR$^a$, —SR$^a$, —CN, —NR$^a$R$^b$ group, —R$^a$ and —R$^b$ being as defined above, R$_6$ represents a hydrogen atom or a —CH$_3$, —CH$_2$—CN, —CH$_2$—SR$^a$, —CH$_2$—SeR$^a$ group or also a group corresponding to formula (A) or (B) below:

—CH$_2$-Q-R$^c$ (A)

or

—C(O)-Q-R$^c$ (B)

in which
Q represents an oxygen atom or an —NR$^a$ group in which R$^a$ is as defined above, or a spacer arm constituted by a linear or branched hydrocarbon chain, optionally substituted, of 2 to 20 carbon atoms and with at least one heteroatom,
R$^c$ represents a hydrogen atom or a C$_1$-C$_6$ alkyl, or aryl, or heteroaryl group, or a heterocycle, or C$_1$-C$_6$ alkyl-C(O)—, or aryl-C(O)—, or heteroaryl-C(O)—, or heterocycle-C(O)—, or a group represented by one of formulae (C) or (D)

(C)

(D)

R$_7$ represents a hydrogen atom or a halogen atom or a hydroxy group;

R$_8$ represents a hydrogen atom, or an —OR$^a$ group, R$^a$ being as defined above;

R$_9$ represents a hydrogen atom, or a C$_1$-C$_6$ alkyl, C$_3$-C$_6$ cycloalkyl, C$_2$-C$_6$ alkenyl, C$_2$-C$_6$ alkynyl, aryl group or a halogen atom;

R$_{10}$ represents a hydrogen atom, or a C$_1$-C$_6$ alkyl group, a halogen atom or a —CN, —CF$_3$, —NO$_2$, —OR$^a$, —SR$^a$, —SO$_2$R$^a$, —NR$^a$R$^b$, —OC(O)R$^a$, —OC(O)NR$^a$R$^b$, —C(O)OR$^a$, —C(O)NR$^a$R$^b$ group, R$^a$ and R$^b$ being as defined above; or R$_{10}$ represents, together with R$_9$, an oxo, =CH—C$_1$-C$_6$ alkyl, =CH-aryl, or =CH—(C$_3$-C$_6$)-cycloalkyl group;

R$_{11}$ represents a hydrogen atom or a C$_1$-C$_6$ alkyl, C$_3$-C$_6$ cycloalkyl or aryl group; or R$_{11}$ and R$_9$ together form an additional C—C bond between the carbon atoms to which they are attached, or together form a C$_3$-C$_6$ cycloalkyl group;

R$_{12}$ represents a hydrogen atom or a C$_1$-C$_6$ alkyl group, or an —OR$^a$, or an —SR$^a$ group, with R$^a$ being as defined above, as well as:
its SYN, ANTI isomers,
its optical isomers (enantiomers, diastereoisomers),
its addition salts with a pharmaceutically acceptable acid or base,
with the proviso that the compound is not one of the following compounds:
3-oxyimino-4-chloro-cholest-4-ene;
3-oxyimino-4-bromo-cholest-4-ene;
3-oxyimino-4-methyl-cholest-4-ene.

2. The compound according to claim 1, wherein $R_1$ represents a hydrogen atom.

3. The compound according to claim 1, wherein $R_1$ represents a $C_1$-$C_6$ alkyl group.

4. The compound according to claim 1, wherein $R_1$ represents a fluorine atom.

5. The compound according to claim 1, wherein $R_1$ represents a phenyl, optionally substituted.

6. The compound according to claim 1, wherein $R_6$ is a $CH_3$ group or a $CH_2$—OH group.

7. The compound according to claim 1, wherein $R_6$ represents a group corresponding to formula (A) below:

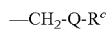
(A)

in which Q represents an oxygen atom and $R^c$ represents a group corresponding to formula (C)

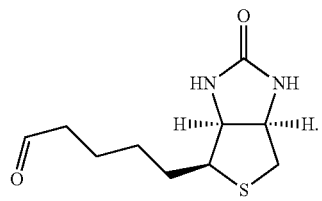
(C)

8. The compound according to claim 1, wherein it corresponds to formula (I) in which $R_4$ together with $R_2$ forms an additional C—C bond between the carbon atoms to which $R_2$ and $R_4$ are attached.

9. The compound according to claim 1, wherein it corresponds to formula (I) in which $R_{11}$ together with $R_9$ forms an additional C—C bond between the carbon atoms to which $R_{11}$ and $R_9$ are attached.

10. The compound according to claim 1, wherein $R_7$ is a hydrogen atom.

11. The compound according to claim 1, wherein $R_8$ is a hydrogen atom.

12. The compound according to claim 1, wherein $R_7$ and $R_8$ are hydrogen atoms.

13. The compound according to claim 1, wherein $R_9$ is a hydrogen atom.

14. The compound according to claim 1, wherein $R_{10}$ is a hydrogen atom.

15. The compound according to claim 1, wherein $R_{11}$ is a hydrogen atom.

16. The compound according to claim 1, wherein $R_{12}$ is a hydrogen atom.

17. The compound according to claim 1, wherein $R_9$, $R_{10}$, $R_{11}$ and $R_{12}$ are hydrogen atoms.

18. The compound according to claim 1, wherein $R_6$ is a methyl.

19. The compound according to claim 1, wherein $R_{13}$ represents a group selected from the group consisting of

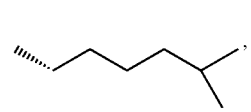
$G_1$

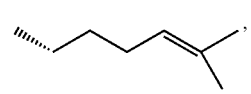
$G_2$

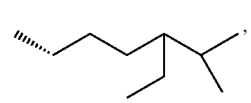
$G_3$

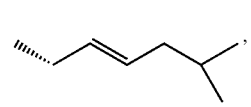
$G_4$

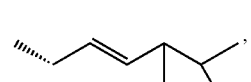
$G_5$

$G_6$

20. The compound according to claim 19, wherein $R_{13}$ =$G_1$

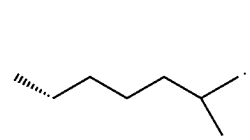
$G_1$

21. The compound according to claim 19, wherein $R_{13}$ =$G_2$

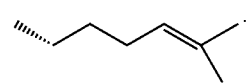
$G_2$

22. The compound according to claim 1, wherein $R_{13}$ represents a group corresponding to formula (E) below:

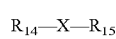
(E)

in which $R_{14}$ represents a $C_5$-$C_{10}$ alkyl group.

23. The compound according to claim 1, wherein $R_{13}$ represents a group corresponding to formula (E) below:

(E)

in which R$_{15}$ represents a group of the formula (C) or (D)

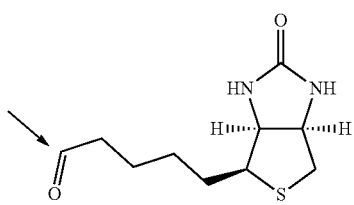
(C)

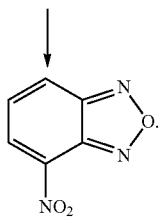
D

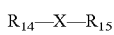

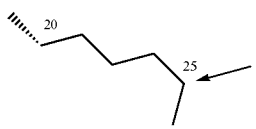

24. The compound according to claim 1, wherein R$_{13}$ represents a group corresponding to formula (E) below:

R$_{14}$—X—R$_{15}$ (E)

in which:
R$_{14}$ represents the G$_7$ group below

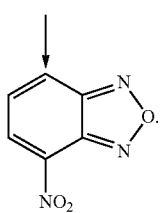
G$_7$

X represents NH or NCH$_3$, and
R$_{15}$ represents a group selected from the groups consisting of aryl, heteroaryl, and heterocycle.

25. The compound according to claim 1, wherein R$_{15}$ represents the group of formula (D) below:

D

26. The compound according to claim 1, wherein R$_{13}$ represents a group corresponding to formula (E) below:

R$_{14}$—X—R$_{15}$ (E)

in which
R$_{14}$ represents the G$_7$ group below

G$_7$

X represents NH or NCH$_3$, and
R$_{15}$ represents the group corresponding to formula (C) below

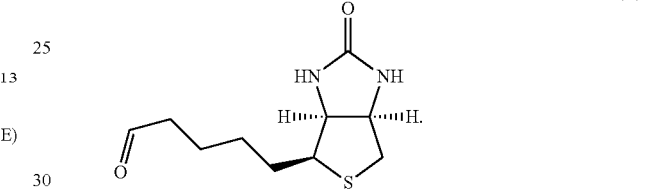
(C)

27. The compound according to claim 1, selected from the group consisting of:
3-oxyimino-4-fluoro-cholest-4-ene,
3-oxyimino-6β-fluoro-cholest-4-ene,
3-oxyimino-2,2-difluoro-cholest-4-ene,
3-oxyimino-2,6-difluoro-cholest-4-ene,
3-oxyimino-2α-fluoro-cholest-4-ene,
3-oxyimino-25-[methyl(7-nitro-2,1,3-benzoxadiazol-4-yl)amino]-27-norcholest-4-ene,
3-oxyimino-25-((N-(+)-biotinoyl-N-methyl) amino)-27-norcholest-4-ene,
3-oxyimino-19-hydroxy-cholest-4-ene,
3-oxyimino-19-biotinyloxy-cholest-4-ene,
3-oxyimino-2-methyl-cholest-4-ene, and
3-oxyimino-4-methoxy-cholest-4-ene.

28. The compound according to claim 1, wherein R1 represents a C$_1$-C$_4$ alkyl group.

29. A pharmaceutical composition, comprising the compound of claim 1 and a pharmaceutically acceptable excipient.

* * * * *